(12) United States Patent
Chung et al.

(10) Patent No.: US 10,550,432 B2
(45) Date of Patent: Feb. 4, 2020

(54) METHOD FOR PREDICTING RISK OF ANKYLOSING SPONDYLITIS USING DNA COPY NUMBER VARIANTS

(71) Applicant: Catholic University Industry Academic Cooperation Foundation, Seoul (KR)

(72) Inventors: Yeun-Jun Chung, Gyeonggi-do (KR); Tae-Hwan Kim, Seoul (KR); Seung Cheol Shim, Daejeon (KR); Seung-Hyun Jung, Seoul (KR)

(73) Assignee: CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 156 days.

(21) Appl. No.: 15/307,555

(22) PCT Filed: Sep. 30, 2014

(86) PCT No.: PCT/KR2014/009209
§ 371 (c)(1),
(2) Date: Oct. 28, 2016

(87) PCT Pub. No.: WO2015/167087
PCT Pub. Date: Nov. 5, 2015

(65) Prior Publication Data
US 2017/0204463 A1   Jul. 20, 2017

(30) Foreign Application Priority Data

Apr. 29, 2014 (KR) .................. 10-2014-0051987
Sep. 29, 2014 (KR) .................. 10-2014-0130306

(51) Int. Cl.
*C12Q 1/6883* (2018.01)
(52) U.S. Cl.
CPC ...... *C12Q 1/6883* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 2010/0203051 A1* | 8/2010 | Brown ............... C12Q 1/6883 |
| --- | --- | --- |
| | | 424/134.1 |
| 2012/0148574 A1 | 6/2012 | Brown et al. ............. 424/133.1 |
| 2013/0172206 A1 | 7/2013 | Uddin et al. ..................... 506/9 |
| 2014/0099641 A1 | 4/2014 | Nam et al. ................... 435/6.12 |

FOREIGN PATENT DOCUMENTS

| KR | 1020080072643 | 8/2008 |
| --- | --- | --- |
| WO | WO 2013060005 | 5/2013 |

OTHER PUBLICATIONS

Jung et al Arthritis & Rheumatology. Online Apr. 2014. 66(8): 2103-2112 and Supplementary Data.*
Lin et al Nature Genetics. Online Dec. 4, 2011. 44(1). 73-77 and "Online Methods".*
Klopocki et al Annual Reviews Genomics Human Genetics. 2011. 12: 53-72.*
Wang et al PLoS ONE. May 11, 2017. 12(5): e0177080.*
Evans et al., *Nature Genetics* 43.8 (2011): 761-767.
Jung et al., *Arthritis & Rheumatology* 66.8 (2014): 2013-2112.
Lin et al., *Nature Genetics* 44.1 (2012): 73-77.
Wang et al., *Genes Immun.* 14.8 (2013): doi:10.1038/gene.2013.46.

* cited by examiner

*Primary Examiner* — Carla J Myers
(74) *Attorney, Agent, or Firm* — Norton Rose Fulbright US LLP

(57) ABSTRACT

The present invention relates to a method of predicting the risk of developing ankylosing spondylitis using DNA copy number variation. It was verified that the risk of developing ankylosing spondylitis can be effectively predicted using primers for detecting DNA copy number variation, of the present invention, and the sensitivity and specificity of prediction can be improved by grafting the results of single nucleotide polymorphism (SNP) measurements, and thus more fundamental approaches for preventing and treating ankylosing spondylitis are expected.

2 Claims, 13 Drawing Sheets
Specification includes a Sequence Listing.

[Fig.6]
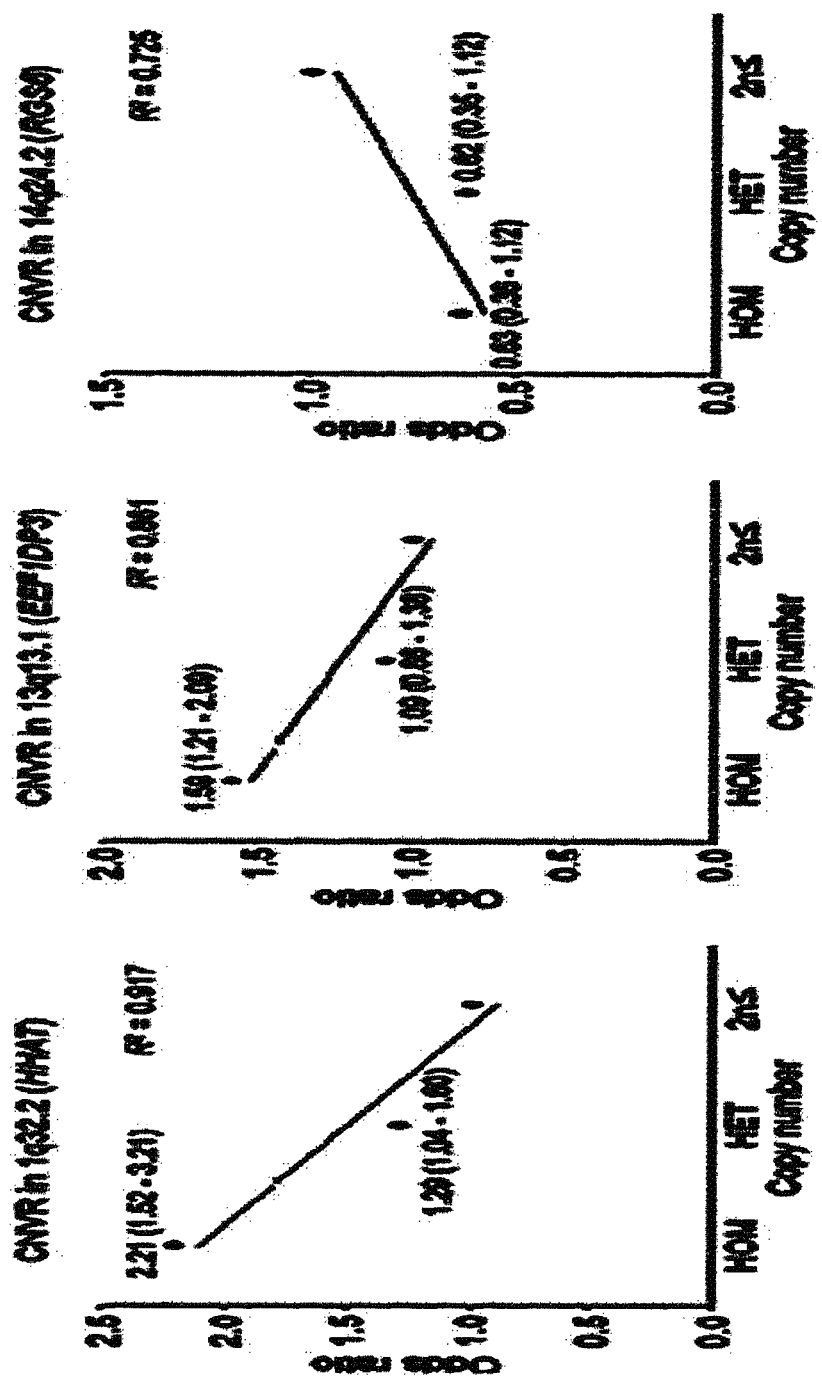

[Fig.7]
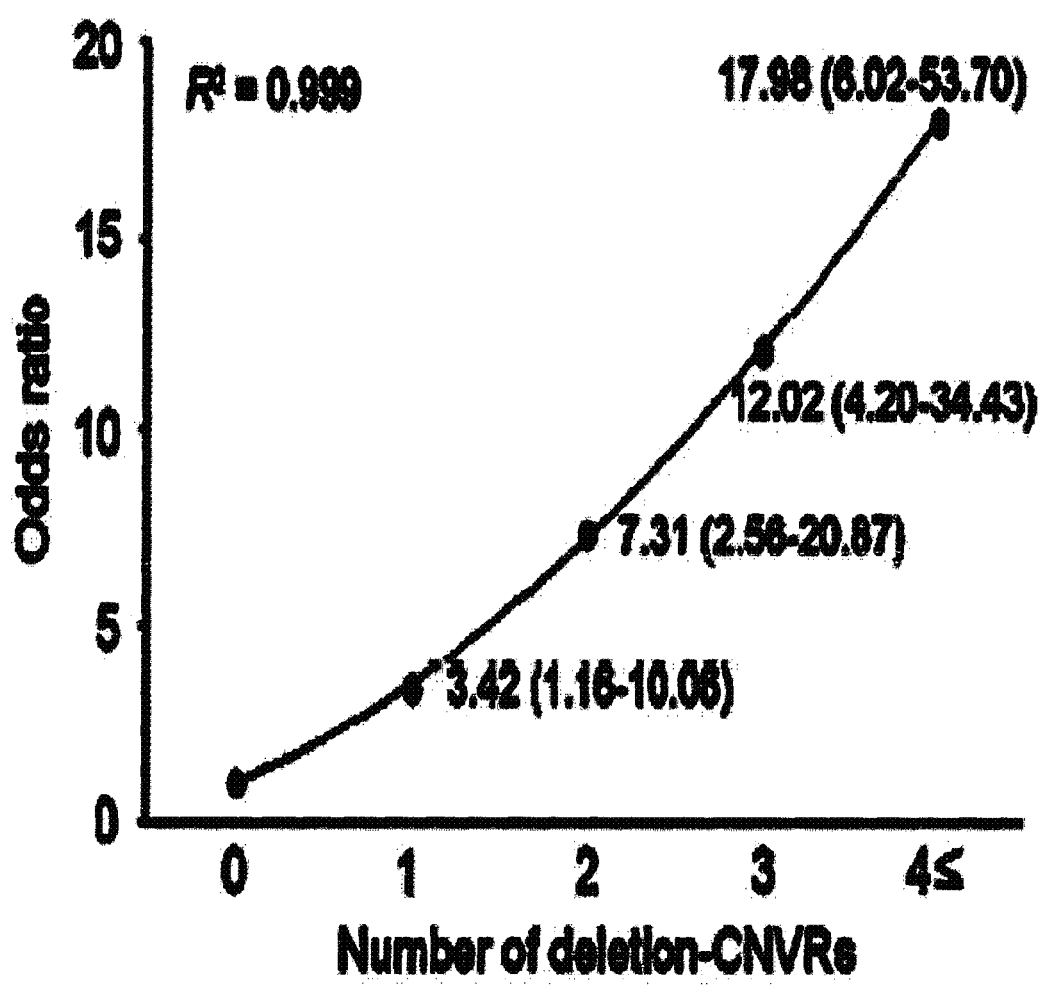

[Fig.8]
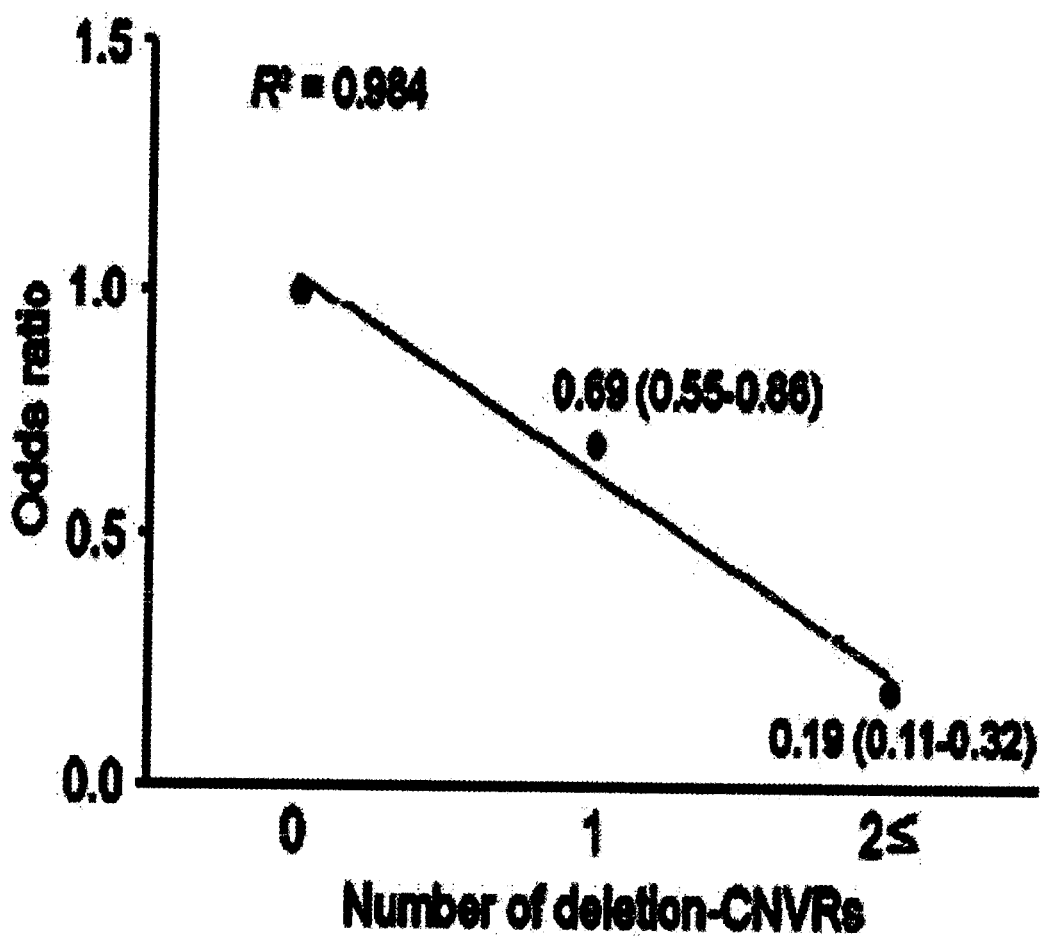

[Fig.9]
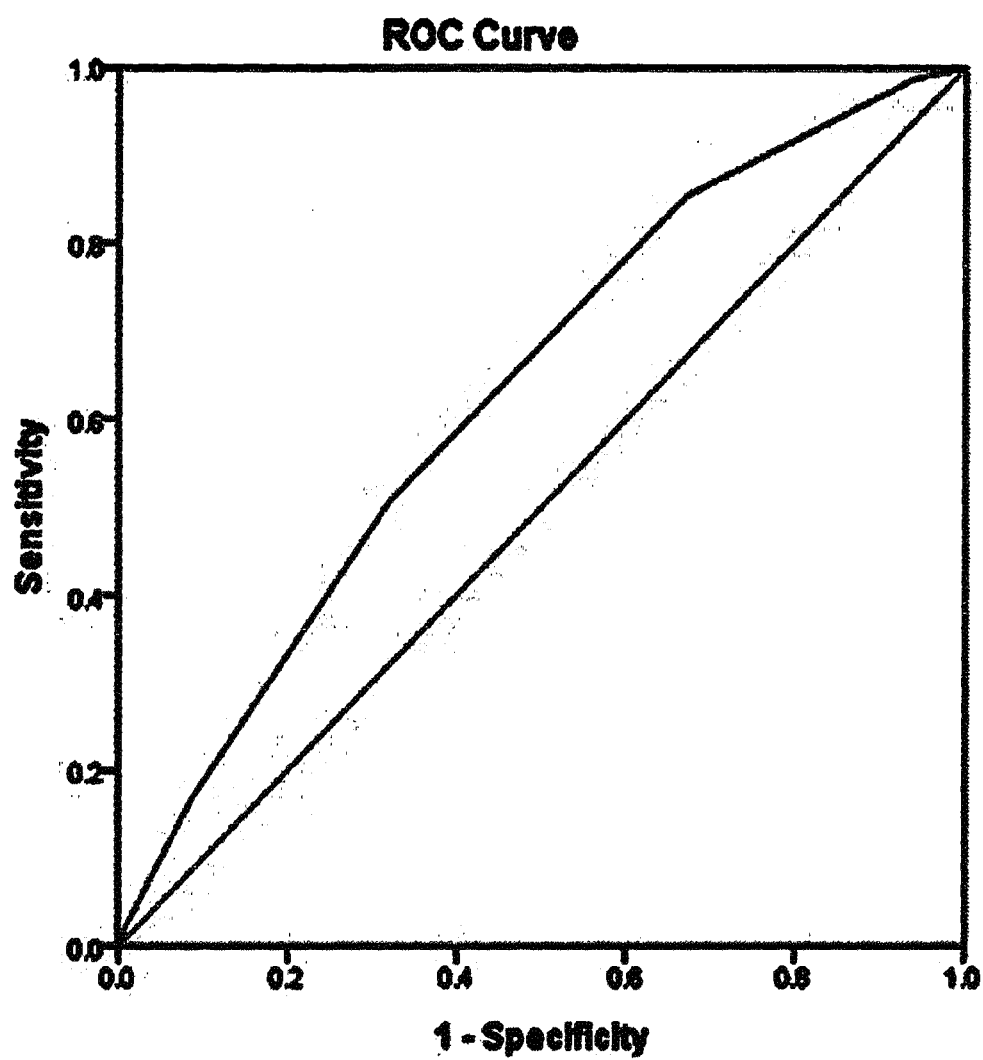

[Fig.10]
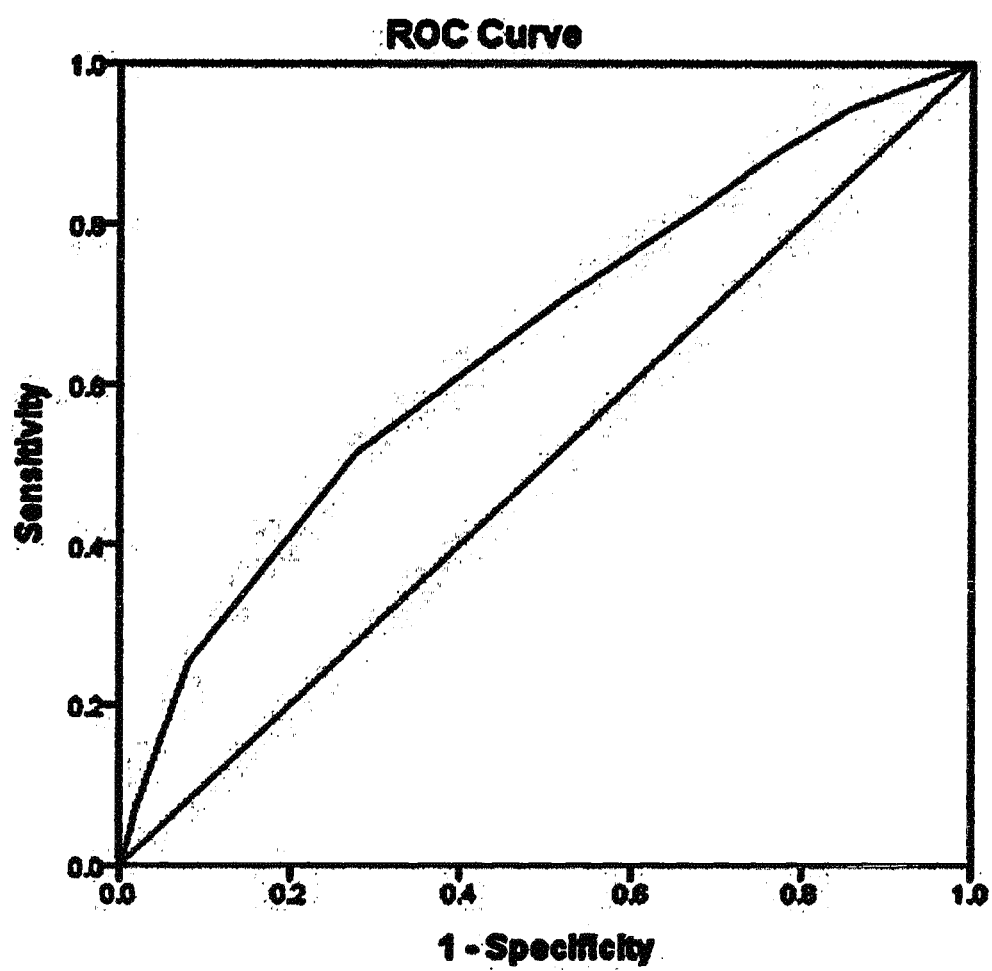

[Fig.11]
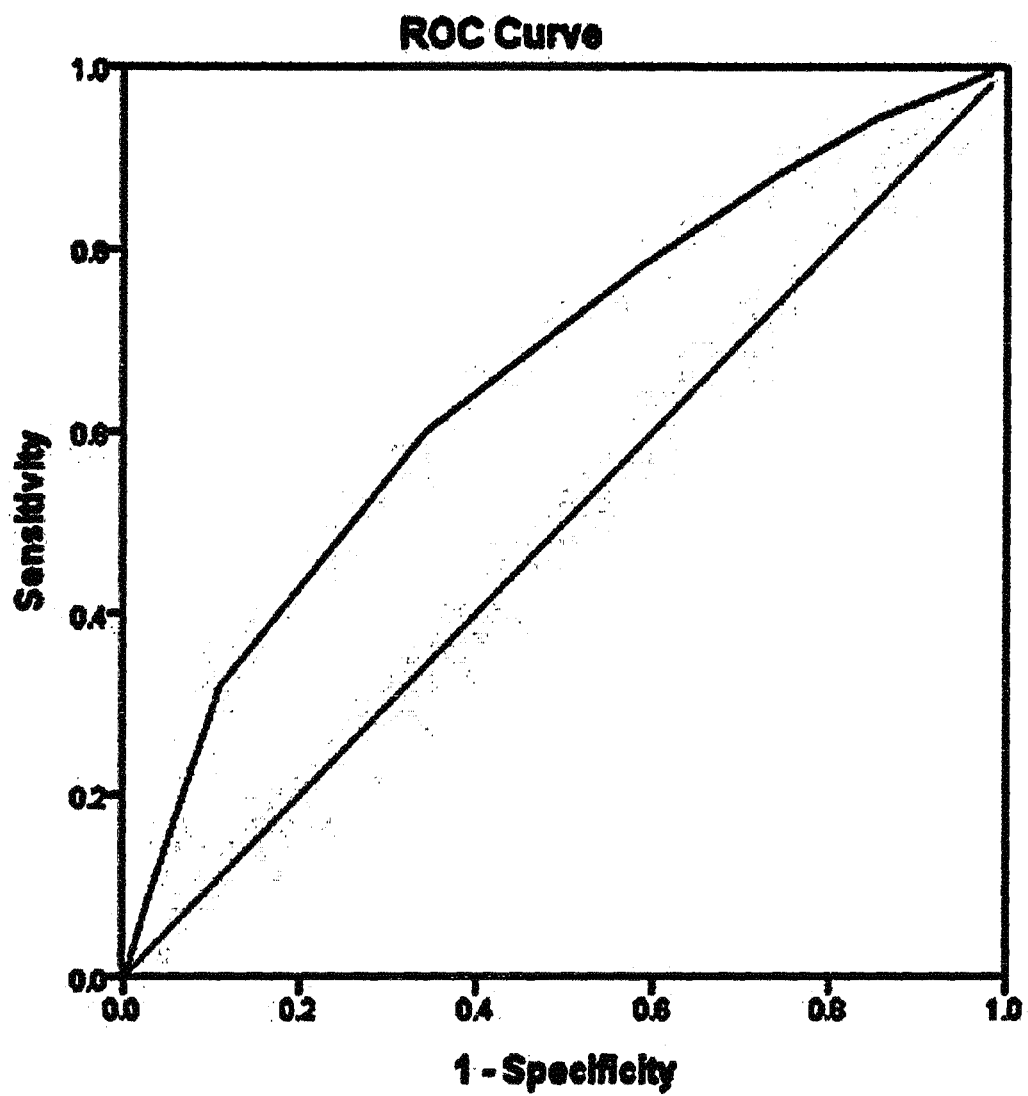

[Fig.12]
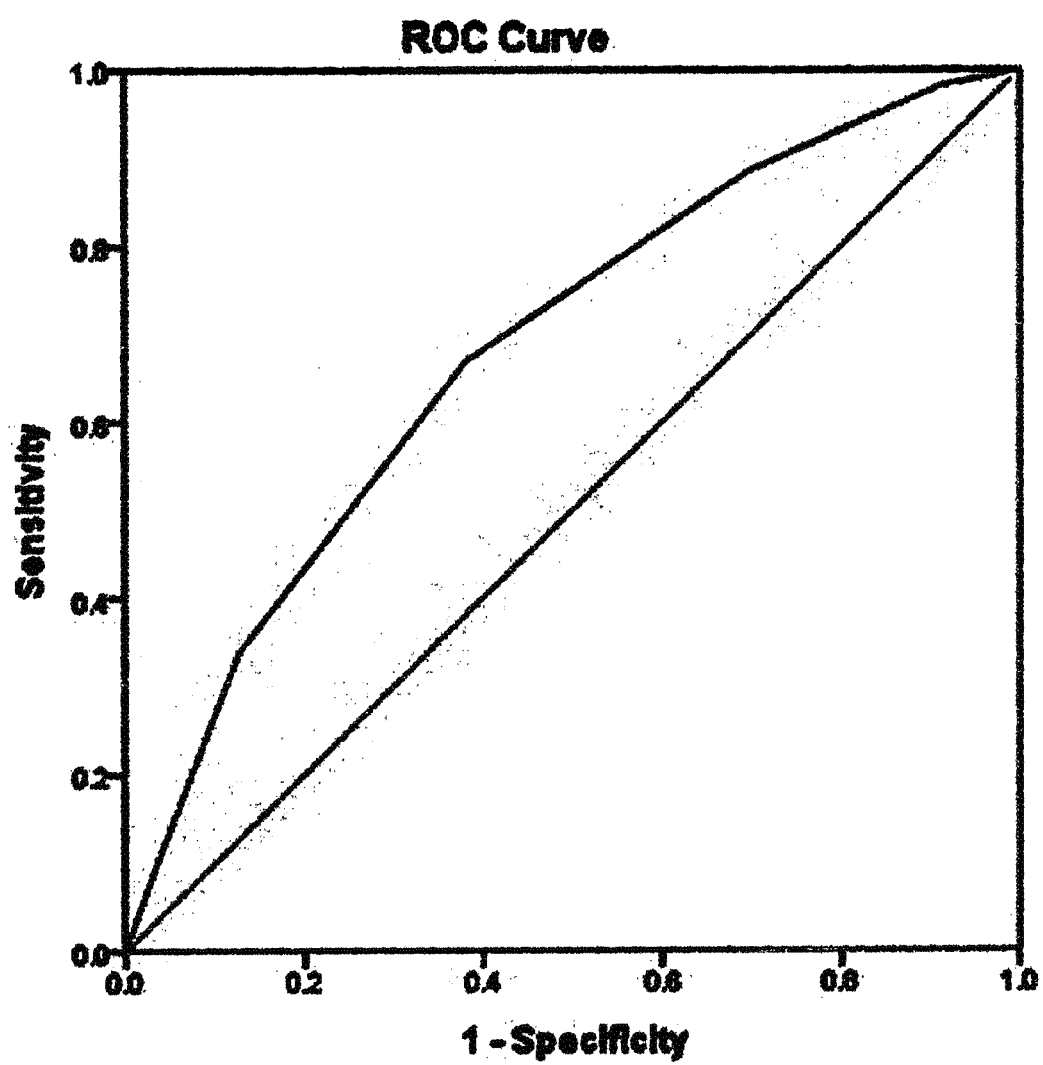

[Fig.13]
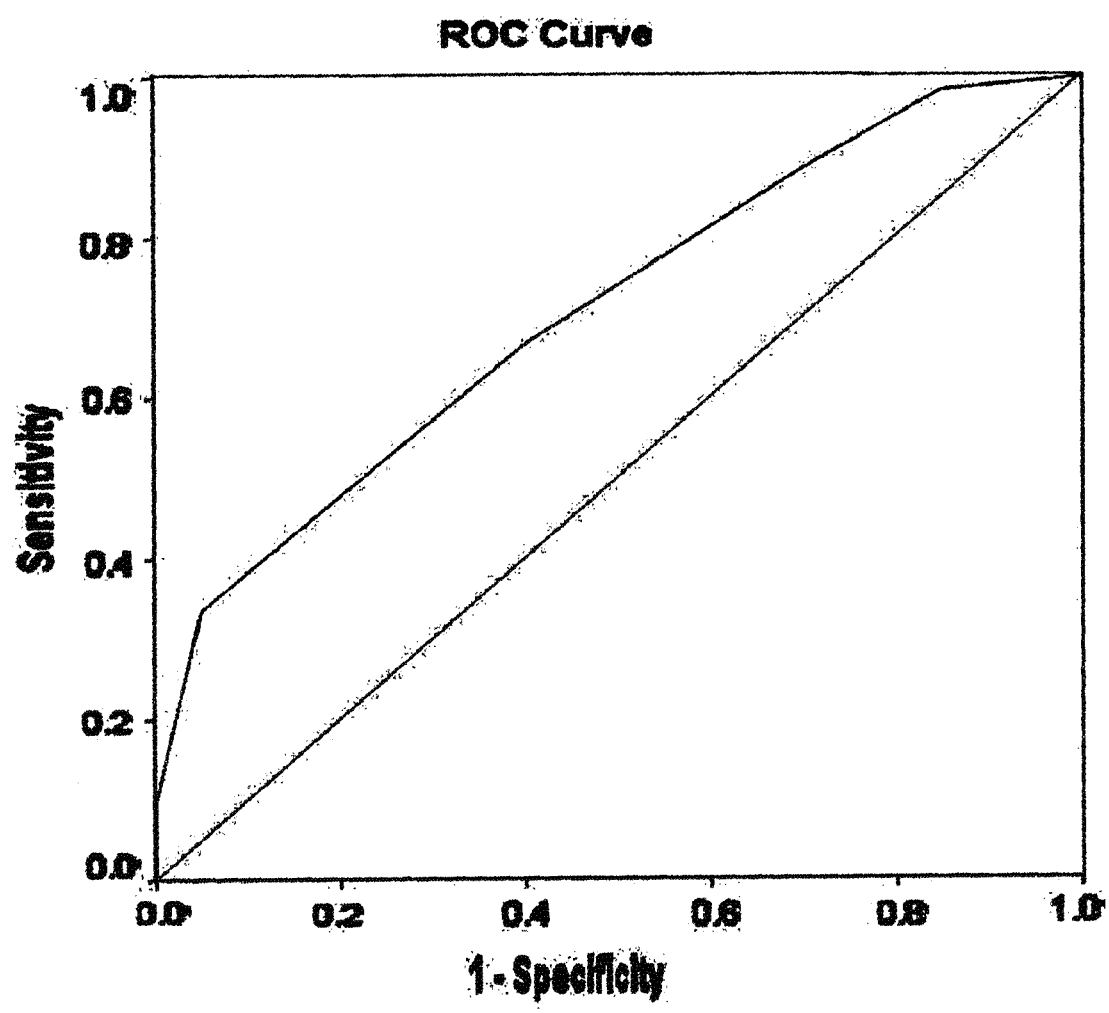

METHOD FOR PREDICTING RISK OF ANKYLOSING SPONDYLITIS USING DNA COPY NUMBER VARIANTS

CROSS-REFERENCE TO RELATED APPLICATIONS

This application is a national phase application under 35 U.S.C. § 371 of International Application No. PCT/KR2014/009209 filed Sep. 30, 2014, which claims priority to Republic of Korea Patent Application No. 10-2014-0051987 filed Apr. 29, 2014, and Republic of Korea Patent Application No. 10-2014-0130306 filed Sep. 29, 2014. The entire contents of each of the above-referenced disclosures are specifically incorporated herein by reference without disclaimer.

TECHNICAL FIELD

The present invention relates to a method of predicting the risk of developing ankylosing spondylitis (AS), and more particularly to a method of predicting the risk of developing ankylosing spondylitis by identifying DNA copy number variation (CNV) at specific chromosomal locations.

BACKGROUND ART

As a form of severe spondyloarthritis (SpA), ankylosing spondylitis (AS) develops in the late teens to early twenties and exhibits symptoms, such as typical spondylosis, in the thirties to forties and is considered as a chronic progressive systemic disease characterized by chronic inflammation of the sacroiliac joints and spine and invasion into the peripheral joints, eyes, heart, or intestine. Although the prevalence rate of spondyloarthritis varies by country, the rate is generally 1 to 2%, and spondyloarthritis has adverse socioeconomic effects on patients and society due to restricted patient mobility.

Although the causes of ankylosing spondylitis are not yet clearly understood, it is assumed that genetic abnormalities, infections, and inflammatory responses may be involved in the onset of ankylosing spondylitis, similar to the case of systemic rheumatic diseases such as rheumatoid arthritis and systemic lupus erythematosus. It is thought that HLA-B27, a histocompatibility antigen gene, is genetically involved in the onset of ankylosing spondylitis, and a recent study also showed the involvement of endoplasmic reticulum aminopeptidase 1 (ERAP1) and interleukin 23 receptor (IL23R) genes in the onset of ankylosing spondylitis. Pain associated with ankylosing spondylitis starts slowly in the waist and sacrum, and arthritis intermittently occurs in the knees, ankles, and so forth in some cases. Since symptoms of ankylosing spondylitis are ambiguous and aggravation and relief of the symptoms occur repeatedly, ankylosing spondylitis is difficult to distinguish from general lower back pain or unspecific arthralgia. According to a study in Europe, average time from appearance of spondyloarthritis symptoms to diagnosis of ankylosing spondylitis is about 10 years. Accordingly, patients visit medical specialists after ankylosing spondylitis has somewhat advanced, but by that time, the patients often have missed the point of initial treatment for the disease.

On the basis of newly accumulated knowledge about progression and treatment of ankylosing spondylitis, early treatment has recently been revealed to be effective in suppressing disease progression, and thus early diagnosis and prediction of the onset of the disease have emerged as important issues. Accordingly, prediction of the onset of ankylosing spondylitis has become a subject of major research projects, and thus research on the subject, e.g., Korea Patent Application Publication No. 10-2008-0072643, has been conducted. However, there is much more to be investigated. As a form of severe spondyloarthritis (SpA), ankylosing spondylitis (AS) develops in the late teens to early twenties and exhibits symptoms, such as typical spondylosis, in the thirties to forties, and is considered as a chronic progressive systemic disease characterized by chronic inflammation of the sacroiliac joints and spine and invasion into the peripheral joints, eyes, heart, or intestine. Although the prevalence rate of spondyloarthritis varies by country, the rate is generally 1 to 2%, and spondyloarthritis has adverse socioeconomic effects on patients and society due to restricted patient mobility.

Although the causes of ankylosing spondylitis are not yet clearly understood, it is assumed that genetic abnormalities, infections, and inflammatory responses may be involved in the onset of ankylosing spondylitis, similar to the case of systemic rheumatic diseases such as rheumatoid arthritis and systemic lupus erythematosus. It is thought that HLA-B27, a histocompatibility antigen gene, is genetically involved in the onset of ankylosing spondylitis, and a recent study also showed the involvement of endoplasmic reticulum aminopeptidase 1 (ERAP1) and interleukin 23 receptor (IL23R) genes in the onset of ankylosing spondylitis. Pain associated with ankylosing spondylitis starts slowly in the waist and sacrum, and arthritis intermittently occurs in the knees, ankles, and so forth in some cases. Since symptoms of ankylosing spondylitis are ambiguous and aggravation and relief of the symptoms occur repeatedly, ankylosing spondylitis is difficult to distinguish from general lower back pain or unspecific arthralgia. According to a study in Europe, average time from appearance of spondyloarthritis symptoms to diagnosis of ankylosing spondylitis is about 10 years. Accordingly, patients visit medical specialists after ankylosing spondylitis has somewhat advanced, but by that time, the patients often have missed the point of initial treatment for the disease.

On the basis of newly accumulated knowledge about progression and treatment of ankylosing spondylitis, early treatment has recently been revealed to be effective in suppressing disease progression, and thus early diagnosis and prediction of the onset of disease have emerged as important issues. Accordingly, prediction of the onset of ankylosing spondylitis has become a subject of major research projects, and thus research on the subject, e.g., Korea Patent Application Publication No. 10-2008-0072643, has been conducted. However, there is much more to be investigated.

DISCLOSURE

Technical Problem

Therefore, the present invention has been made in view of the above problems. As a result of researching a method of predicting the risk of developing ankylosing spondylitis, the inventors of the present invention verified that the onset of ankylosing spondylitis correlates with DNA copy number variation at specific chromosomal locations, and thus completed the present invention on the basis of the result.

Thus, an objective of the present invention is to provide a marker composition for predicting the risk of developing ankylosing spondylitis using DNA copy number variation.

Another objective of the present invention is to provide a method of predicting the risk of developing ankylosing spondylitis using DNA copy number variation.

Another objective of the present invention is to provide a composition for predicting the risk of developing ankylosing spondylitis, the composition including primers for detecting DNA copy number variation.

Yet another objective of the present invention is to provide a kit for predicting the risk of developing ankylosing spondylitis, the kit including primers for detecting DNA copy number variation.

However, the technical problems that are intended to be achieved in the present invention are not restricted to the above described problems, and other problems, which are not mentioned herein, could be clearly understood by those of ordinary skill in the art from the details described below.

Technical Solution

In order to accomplish the above objectives of the present invention, the present invention provides a marker composition for predicting the risk of developing ankylosing spondylitis, including a combination of genetic markers at chromosome 1q32.2, 2q31.2, 6p21.32, 13q13.1, and 16p13.3 loci.

In an embodiment of the present invention, the marker composition of the present invention may further include a combination of single nucleotide polymorphism (SNP) markers, rs10865331 and rs27044.

The present invention provides a method of predicting the risk of developing ankylosing spondylitis, the method including: (a) a step of performing PCR on the genomic DNA samples of clinical specimens, wherein the genomic DNA samples have been treated with a primer set for detecting DNA copy number variation; (b) a step of performing sequencing of the PCR products; and (c) a step of determining whether DNA copy number variation exists in the clinical specimens, based on the performed sequencing results.

In an embodiment of the present invention, the primer set in step (a) may be selected from the group consisting of: a primer set for detecting DNA copy number variation on chromosome 1p34.2, wherein the primer set is composed of sequence No. 1 as a forward primer and sequence No. 2 as a reverse primer; a primer set for detecting DNA copy number variation on chromosome 1q32.2, wherein the primer set is composed of sequence No. 3 as a forward primer and sequence No. 4 as a reverse primer; a primer set for detecting DNA copy number variation on chromosome 2q31.2, wherein the primer set is composed of sequence No. 5 as a forward primer and sequence No. 6 as a reverse primer; a primer set for detecting DNA copy number variation on chromosome 6p21.32, wherein the primer set is composed of sequence No. 7 as a forward primer and sequence No. 8 as a reverse primer; a primer set for detecting DNA copy number variation on chromosome 11q22.1, wherein the primer set is composed of sequence No. 9 as a forward primer and sequence No. 10 as a reverse primer; a primer set for detecting DNA copy number variation on chromosome 13q13.1, wherein the primer set is composed of sequence No. 11 as a forward primer and sequence No. 12 as a reverse primer; a primer set for detecting DNA copy number variation on chromosome 14q24.2, wherein the primer set is composed of sequence No. 13 as a forward primer and sequence No. 14 as a reverse primer; a primer set for detecting DNA copy number variation on chromosome 16p13.3, wherein the primer set is composed of sequence No. 15 as a forward primer and sequence No. 16 as a reverse primer; a primer set for detecting DNA copy number variation on chromosome 22q11.1, wherein the primer set is composed of sequence No. 17 as a forward primer and sequence No. 18 as a reverse primer; a primer set for detecting DNA copy number variation on chromosome 1q32.2, wherein the primer set is composed of sequence No. 21 as a forward primer and sequence No. 22 as a reverse primer; a primer set for detecting DNA copy number variation on chromosome 13q13.1, wherein the primer set is composed of sequence No. 23 as a forward primer and sequence No. 24 as a reverse primer; and a primer set for detecting DNA copy number variation on chromosome 14q24.2, wherein the primer set is composed of sequence No. 25 as a forward primer and sequence No. 26 as a reverse primer.

In another embodiment of the present invention, the PCR in step (a) may be genomic quantitative PCR or deletion-typing PCR.

In another embodiment of the present invention, when DNA copy number variation exists at any one or more loci selected from the group consisting of chromosome 1p34.2, 11q22.1, 14q24.2, and 22q11.1 loci, a subject with the DNA copy number variation may be predicted as belonging in a low-risk group for onset of ankylosing spondylitis.

In another embodiment of the present invention, when DNA copy number variation exists at any one or more loci selected from the group consisting of chromosome 1q32.2, 2q31.2, 6p21.32, 13q13.1, and 16p13.3 loci, a subject with the DNA copy number variation may be predicted as belonging in a high-risk group for onset of ankylosing spondylitis.

In another embodiment of the present invention, the method of the present invention may further include: (d) a step of performing polymerase chain reaction (PCR) on the genomic DNA samples of clinical specimens, wherein the genomic DNA samples have been treated with a primer set for detecting a single nucleotide polymorphism; and (e) a step of determining whether a single nucleotide polymorphism exists in the PCR products.

In another embodiment of the present invention, the primer set in step (d) may be selected from the group consisting of: a primer set for detecting a single nucleotide polymorphism, wherein the primer set specifically binds to an SNP marker, rs10865331, composed of sequence No. 29; and a primer set for detecting a single nucleotide polymorphism, wherein the primer set specifically binds to an SNP marker, rs27044, composed of sequence No. 30.

In yet another embodiment of the present invention, when a single nucleotide polymorphism exists at any one or more selected from the group consisting of rs10865331 and rs27044 on the chromosome, a subject with the single nucleotide polymorphism may be predicted as belonging in a high-risk group for onset of ankylosing spondylitis.

The present invention provides a composition for predicting the risk of developing ankylosing spondylitis, the composition including any one or more primer sets selected from the group consisting of: a primer set for detecting DNA copy number variation on chromosome 1p34.2, wherein the primer set is composed of sequence No. 1 as a forward primer and sequence No. 2 as a reverse primer; a primer set for detecting DNA copy number variation on chromosome 1q32.2, wherein the primer set is composed of sequence No. 3 as a forward primer and sequence No. 4 as a reverse primer; a primer set for detecting DNA copy number variation on chromosome 2q31.2, wherein the primer set is composed of sequence No. 5 as a forward primer and sequence No. 6 as a reverse primer; a primer set for detecting DNA copy number variation on chromosome 6p21.32, wherein the primer set is composed of sequence No. 7 as a forward primer and sequence No. 8 as a reverse primer; a primer set for detecting DNA copy number variation on chromosome 11q22.1, wherein the primer set is composed of sequence No. 9 as a forward primer and sequence No. 10 as a reverse primer; a primer set for detecting DNA copy number variation on chromosome 13q13.1, wherein the primer set is composed of sequence No. 11 as a forward primer and sequence No. 12 as a reverse primer; a primer set for detecting DNA copy number variation on chromosome 14q24.2, wherein the primer set is composed of sequence No. 13 as a forward primer and sequence No. 14 as a reverse primer; a primer set for detecting DNA copy number variation on chromosome 16p13.3, wherein the primer set is composed of sequence No. 15 as a forward primer and sequence No. 16 as a reverse primer; a primer set for detecting DNA copy number variation on chromosome 22q11.1, wherein the primer set is composed of sequence No. 17 as a forward primer and sequence No. 18 as a reverse primer; a primer set for detecting DNA copy number variation on chromosome 1q32.2, wherein the primer set is composed of sequence No. 21 as a forward primer and sequence No. 22 as a reverse primer; a primer set for detecting DNA copy number variation on chromosome 13q13.1, wherein the primer set is composed of sequence No. 23 as a forward primer and sequence No. 24 as a reverse primer; and a primer set for detecting DNA copy number variation on chromosome 14q24.2, wherein the primer set is composed of sequence No. 25 as a forward primer and sequence No. 26 as a reverse primer.

In an embodiment of the present invention, the composition of the present invention may further include any one or more primer sets selected from the group consisting of: a primer set for detecting a single nucleotide polymorphism, wherein the primer set specifically binds to an SNP marker, rs10865331, composed of sequence No. 29; and a primer set for detecting a single nucleotide polymorphism, wherein the primer set specifically binds to an SNP marker, rs27044, composed of sequence No. 30.

The present invention may provide a kit for predicting the risk of developing ankylosing spondylitis, the kit including the composition of the present invention.

Advantageous Effects

According to the present invention, a method of the present invention includes a step of measuring whether DNA copy number variation exists or not. The risk of developing ankylosing spondylitis was verified to be correlated with DNA copy number variation, in the group having DNA copy number variation. In addition, it was verified that the sensitivity and specificity of prediction of the risk of developing ankylosing spondylitis can be improved by combining the results of single nucleotide polymorphism (SNP) measurements with DNA copy number variation. Thereby, it is expected that ankylosing spondylitis, a representative modern disease, may be effectively prevented and treated through early prediction of the onset of ankylosing spondylitis, according to the present invention.

DESCRIPTION OF DRAWINGS

FIG. 6 illustrates, as the results of deletion typing PCR, odds ratios for the onset rates of AS according to copy number (HOM, HET, 2n) variations of 1q32.2, 13q13.1, and 14q24.2 regions.

FIG. 7 illustrates odds ratios for the onset rates of AS in subjects, who have one or more copy number variations simultaneously occurring in CNVRs that are responsible for increasing the onset rates of AS.

FIG. 8 illustrates odds ratios for the onset rates of AS in the subjects, who have one or more copy number variations simultaneously occurring in CNVRs that are responsible for decreasing the onset rates of AS.

FIG. 9 illustrates a receiver-operating characteristic (ROC) curve of a prediction set for the onset rates of AS using 5 types of CNVRs that increase the onset rates of AS.

FIG. 10 illustrates an ROC curve of a prediction set for the onset rates of AS, using 5 types of CNVRs and 5 types of SNPs (i.e., rs27037, rs27434, rs10865331, rs27044, and rs30187), which increase the onset rates of AS.

FIG. 11 illustrates an ROC curve of a prediction set for the onset rates of AS, using 5 types of CNVRs and 4 types of SNPs (i.e., rs27434, rs10865331, rs27044, and rs30187), which increase the onset rates of AS.

FIG. 12 illustrates an ROC curve of a prediction set for the onset rates of AS, using 5 types of CNVRs and 2 types of SNPs (i.e., rs1086533 1and rs27044), which increase the onset rates of AS.

FIG. 13 illustrates ROC curve analysis for HLA-B27 positive subjects, including 501 AS patients and 30 subjects as a control group, for a combination of 5 types of CNVRs and 2 types of SNP markers.

BEST MODE

Figure 1:
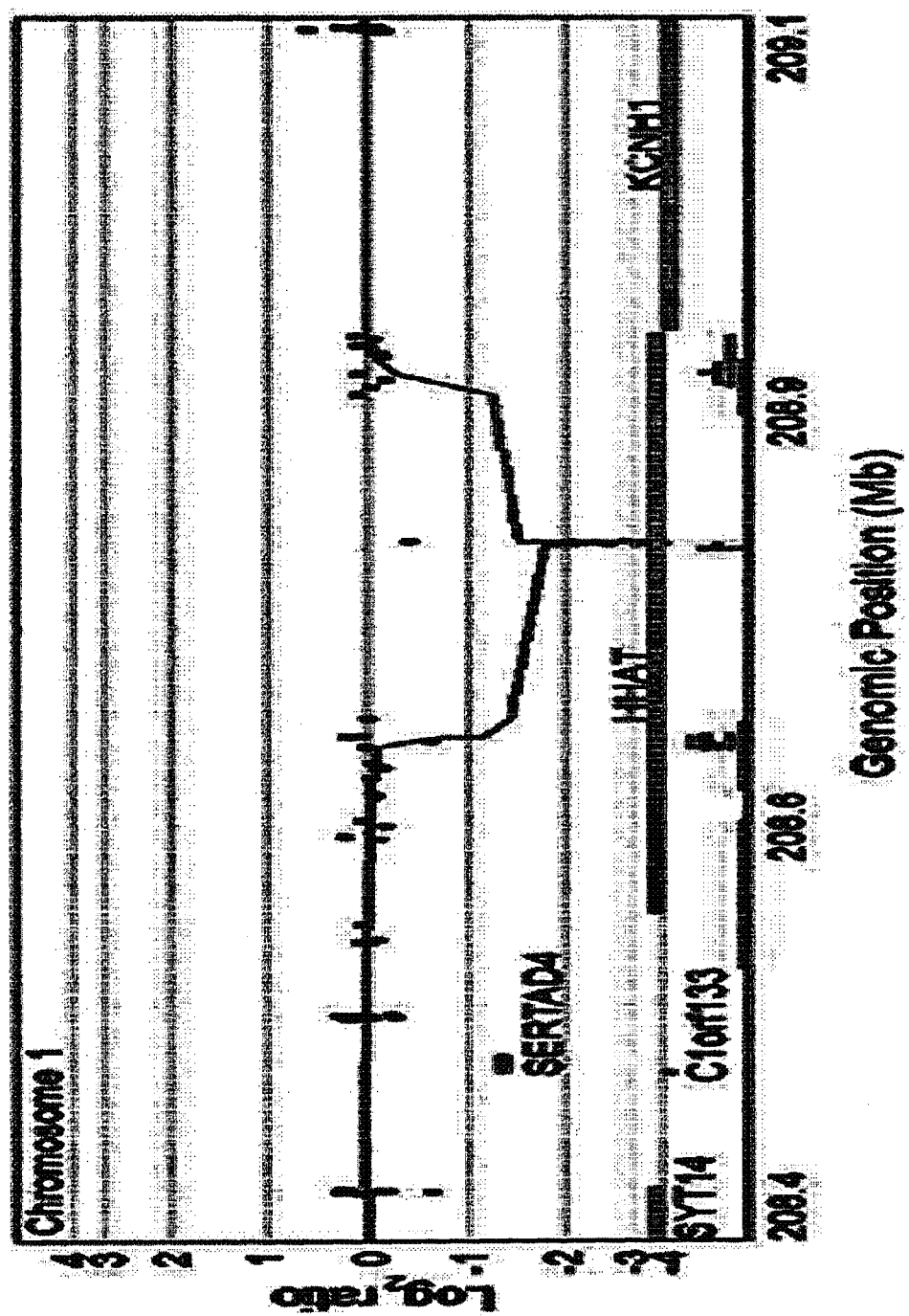
FIG. 1 illustrates the ratios of signal strengths of the 1q32.2 region, in which the ratios are represented as log 2 ratios, as the result of array-CGH experiments.

The present invention provides a marker composition for predicting the risk of developing ankylosing spondylitis, the marker composition including a combination of genetic markers at chromosome 1q32.2, 2q31.2, 6p21.32, 13q13.1, and 16p13.3 loci.

In the present invention, the term "a marker for predicting the risk of developing a disease" includes organic biomolecules, such as polypeptides or nucleic acids (e.g., mRNA, etc.), lipids, glycolipids, glycoproteins, sugars (monosaccharides, disaccharides, oligosaccharides, etc.), etc., the expression levels of genes or proteins of which significantly increase or decrease in individuals at high risk of developing ankylosing spondylitis compared to individuals of a normal control group.

In addition, the marker composition of the present invention may further include a combination of single nucleotide polymorphism (SNP) markers, rs10865331 and rs27044, to improve the sensitivity and specificity of prediction of the risk of developing ankylosing spondylitis.

In the present invention, the term "single nucleotide polymorphism (SNP)" refers to a genetic alteration or variation exhibiting a difference in a single base, i.e., A, T, G, or C, on DNA base sequence, more specifically, referring to a specific position in the genome, wherein two or more alleles occur with some appreciable degree (i.e., >1%) within a population group. According to the present invention, the sensitivity and specificity of prediction of the risk of developing ankylosing spondylitis may be improved by combining the results of DNA copy number variation measurements with the results of single nucleotide polymorphism (SNP) measurements.

The present invention provides a method of predicting the risk of developing ankylosing spondylitis (AS), the method including (a) a step of performing PCR on the genomic DNA samples of clinical specimens, wherein the genomic DNA samples have been treated with a primer set for detecting DNA copy number variation, (b) a step of performing sequencing of the PCR products, and (c) a step of determining whether DNA copy number variation exists in the clinical specimens, based on the performed sequencing results.

In order to predict the risk of developing ankylosing spondylitis, in step (a) of the present invention, the genomic DNA samples of clinical specimens are treated with a primer set for detecting DNA copy number variation, and then subjected to PCR analysis.

In the present invention, the term "DNA copy number variation (CNV)" refers to deletion (On or in) or amplification (3n or more) of a certain base sequence with a length of more than 1 Kb, and is one of the structural variations of a gene along with insertion, deletion, transposition, amplification, translocation, etc. Generally, amplification or deletion of a DNA fragment with a length of more than 1 Kb is considered as CNV. According to a recent result of Wellcome Trust Case Control Consortium (WTCCC), in which CNV correlation analysis was studied, genotype analysis, which is associated with correlation analysis, could be applied to only 40% of total CNV genotypes. In addition, since CNV analysis has poor signal-to-noise ratio, unlike SNP analysis, in the case of WTCCC study, a statistical method was used in predicting CNV genotypes for precise genotyping. According to recent WTCCC studies, use of signal intensity is recommended as an alternative method of predicting CNV genotypes.

In the present invention, the term "polymerase chain reaction (PCR)" refers to a method of amplifying a specific DNA region hundreds of thousands of times by repeating DNA synthesis reaction performed by the action of two kinds of primers covering a specific DNA region and a DNA polymerase in a PCR tube. In general, one cycle of a PCR process consists of a step of separating double-stranded DNA into single strands, i.e., a denaturation step, a step of annealing the separated single-stranded DNA with two kinds of primers covering a target DNA region, i.e., an annealing step, and a step of synthesizing DNA sequences complementary to the target region by extending the primers, i.e., an extension step. In PCR reaction, denaturation of double-stranded DNA is performed at a high temperature, i.e., above 90° C., and primer annealing and DNA synthesis are performed in relatively low temperatures, i.e., 50 to 60° C. and 70 to 76° C., respectively.

In the present invention, the term "primer" refers to oligonucleotides complementary to 5'-terminal and 3'-terminal sequences flanked by target nucleic acids amplified in PCR reaction. The terms "forward primer" and "reverse primer" refer to primers, which respectively bind to 3'-terminal and 5'-terminal sequences of a particular region of a gene, which will be amplified by PCR reaction.

The primer set used in step (a) of the present invention is designed to bind to a particular region of a chromosome harboring DNA copy number variation, and, preferably, may be selected from the group consisting of: a primer set for detecting DNA copy number variation on chromosome 1p34.2, wherein the primer set is composed of sequence No. 1 as a forward primer and sequence No. 2 as a reverse primer; a primer set for detecting DNA copy number variation on chromosome 1q32.2, wherein the primer set is composed of sequence No. 3 as a forward primer and sequence No. 4 as a reverse primer; a primer set for detecting DNA copy number variation on chromosome 2q31.2, wherein the primer set is composed of sequence No. 5 as a forward primer and sequence No. 6 as a reverse primer; a primer set for detecting DNA copy number variation on chromosome 6p21.32, wherein the primer set is composed of sequence No. 7 as a forward primer and sequence No. 8 as a reverse primer; a primer set for detecting DNA copy number variation on chromosome 11q22.1, wherein the primer set is composed of sequence No. 9 as a forward primer and sequence No. 10 as a reverse primer; a primer set for detecting DNA copy number variation on chromosome 13q13.1, wherein the primer set is composed of sequence No. 11 as a forward primer and sequence No. 12 as a reverse primer; a primer set for detecting DNA copy number variation on chromosome 14q24.2, wherein the primer set is composed of sequence No. 13 as a forward primer and sequence No. 14 as a reverse primer; a primer set for detecting DNA copy number variation on chromosome 16p13.3, wherein the primer set is composed of sequence No. 15 as a forward primer and sequence No. 16 as a reverse primer; a primer set for detecting DNA copy number variation on chromosome 22q11.1, wherein the primer set is composed of sequence No. 17 as a forward primer and sequence No. 18 as a reverse primer; a primer set for detecting DNA copy number variation on chromosome 1q32.2, wherein the primer set is composed of sequence No. 21 as a forward primer and sequence No. 22 as a reverse primer; a primer set for detecting DNA copy number variation on chromosome 13q13.1, wherein the primer set is composed of sequence No. 23 as a forward primer and sequence No. 24 as a reverse primer; and a primer set for detecting DNA copy number variation on chromosome 14q24.2, wherein the primer set is composed of sequence No. 25 as a forward primer and sequence No. 26 as a reverse primer.

The PCR in step (a) of the present invention is preferably genomic quantitative PCR or deletion-typing PCR, but the present invention is not limited thereto.

In the present invention, the term "genomic quantitative PCR (qPCR)", as a method of measuring a very small amount of DNA, refers to a method of detecting a fluorescence signal generated during each cycle of PCR reaction. The amount of test DNA sequence introduced by qPCR reaction may determine the intensity of a fluorescence signal generated during cycling, whereby a signal about an amount of DNA sequence is obtained, and then the obtained signal is compared to a signal included in a known standard, and thereby a DNA amount may be accurately quantified over a wide range of concentration.

In the present invention, the term "deletion-typing PCR" is a method of finding an accurate size of a deleted sequence and a deletion breakpoint. The region, which is expected to be deleted, is subjected to the deletion-typing PCR, and then is compared to a deletion region validated by sequencing. In the absence of a deletion, a PCR product exhibits a predicted size. On the other hand, when a deletion is present, a PCR product has a length corresponding to a sequence region excluding the deleted region, thus exhibiting a shortened size.

According to the present invention, in step (b), the PCR product obtained in step (a) is subjected to sequencing for predicting the risk of developing ankylosing spondylitis.

According to the present invention, in order to predict the risk of developing ankylosing spondylitis, in step (c), it is determined whether DNA copy number variation exists in clinical specimens, based on the sequencing results obtained in step (h).

More specifically, when DNA copy number variation exists at any one or more selected from the group consisting of chromosome 1p34.2, 11q22.1, 14q24.2, and 22q11.1 loci, a subject with the DNA copy number variation may be predicted as belonging in a low-risk group for onset of ankylosing spondylitis.

The DNA copy number variation may simultaneously occur at one or more loci, and as the number of deleted CNVRs at chromosome 1p34.2, 11q22.1, 14q24.2 and 22q11.1 loci increases, the onset rate of ankylosing spondylitis decreases.

In addition, when DNA copy number variation exists at any one or more of chromosome 1q32.2, 2q31.2, 6p21.32, 13q13.1, and 16p13.3 loci, the subject with the DNA copy number variation may be predicted as belonging in a high-risk group for onset of ankylosing spondylitis.

The DNA copy number variation may simultaneously occur at one or more loci, and as the number of deleted CNVRs at chromosome 1q32.2, 2q31.2, 6p21.32, 13q13.1, and 16p13.3 loci increases, the onset rate of ankylosing spondylitis increases.

In addition, to improve the sensitivity and specificity of prediction of the risk of developing ankylosing spondylitis, the method of the present invention may further include: (d) a step of performing PCR on the genomic DNA samples of clinical specimens, wherein the genomic DNA samples have been treated with a primer set for detecting a single nucleotide polymorphism; and (e) a step of determining whether a single nucleotide polymorphism exists in the PCR products.

In the present invention, when a single nucleotide polymorphism exists at any one or more selected from the group consisting of rs10865331 and rs27044, a subject with the single nucleotide polymorphism may be predicted as belonging in a high-risk group for onset of ankylosing spondylitis. In addition, the primer set in step (d) of the present invention, which is used to measure whether a single nucleotide polymorphism exists or not, may be selected from the group consisting of a primer set for detecting a single nucleotide polymorphism, wherein the primer set specifically binds to an SNP marker, rs10865331, composed of sequence No. 29; and a primer set for detecting a single nucleotide polymorphism, wherein the primer set specifically binds to an SNP marker, rs27044, composed of sequence No. 30.

According to an example of the present invention, 10 CNVRs associated with AS, wherein the CNVRs include 5 CNVRs responsible for increasing the risk of developing AS and other 5 CNVRs responsible for decreasing the risk of developing AS, were determined and validated by performing array-CGH analysis and qPCR, and after that, the correlation between ankylosing spondylitis and copy number variation of CNVRs was again confirmed through an independent replication method, i.e., qPCR (Examples 1 to 3). In addition, the precise sizes and deletion boundaries of CNVRs were identified by performing deletion-typing PCR, and the correlation between the onset rates of AS and homozygous and heterozygous deletions was verified (Examples 4 to 5). In addition, it was verified that with repeated occurrence of the copy number variation of 5 CNVRs identified in Example 3 responsible for increasing the risk of developing AS, the risk of developing AS greatly increases (Example 6). In addition, it was verified that when a subject has a single nucleotide polymorphism (SNP) associated with the risk of developing AS as well as copy number variation of CNVRs simultaneously, the risk of developing AS further increases. Based on the results, a method of predicting the risk of developing AS with superior sensitivity and specificity was uncovered (Examples 7 to 8).

In another aspect of the present invention, the present invention provides a composition for predicting the risk of developing ankylosing spondylitis, the composition including any one or more primer sets selected from the group consisting of: a primer set for detecting DNA copy number variation on chromosome 1p34.2, wherein the primer set is composed of sequence No. 1 as a forward primer and sequence No. 2 as a reverse primer; a primer set for detecting DNA copy number variation on chromosome 1q32.2, wherein the primer set is composed of sequence No. 3 as a forward primer and sequence No. 4 as a reverse primer; a primer set for detecting DNA copy number variation on chromosome 2q31.2, wherein the primer set is composed of sequence No. 5 as a forward primer and sequence No. 6 as a reverse primer; a primer set for detecting DNA copy number variation on chromosome 6p21.32, wherein the primer set is composed of sequence No. 7 as a forward primer and sequence No. 8 as a reverse primer; a primer set for detecting DNA copy number variation on chromosome 11q22.1, wherein the primer set is composed of sequence No. 9 as a forward primer and sequence No. 10 as a reverse primer; a primer set for detecting DNA copy number variation on chromosome 13q13.1, wherein the primer set is composed of sequence No. 11 as a forward primer and sequence No. 12 as a reverse primer; a primer set for detecting DNA copy number variation on chromosome 14q24.2, wherein the primer set is composed of sequence No. 13 as a forward primer and sequence No. 14 as a reverse primer; a primer set for detecting DNA copy number variation on chromosome 16p13.3, wherein the primer set is composed of sequence No. 15 as a forward primer and sequence No. 16 as a reverse primer; a primer set for detecting DNA copy number variation on chromosome 22q11.1, wherein the primer set is composed of sequence No. 17 as a forward primer and sequence No. 18 as a reverse primer; a primer set for detecting DNA copy number variation on chromosome 1q32.2, wherein the primer set is composed of sequence No. 21 as a forward primer and sequence No. 22 as a reverse primer; a primer set for detecting DNA copy number variation on chromosome 13q13.1, wherein the primer set is composed of sequence No. 23 as a forward primer and sequence No. 24 as a reverse primer; and a primer set for detecting DNA copy number variation on chromosome 14q24.2, wherein the primer set is composed of sequence No. 25 as a forward primer and sequence No. 26 as a reverse primer.

In another aspect of the present invention, the present invention provides a kit for predicting the risk of developing ankylosing spondylitis, wherein the kit includes the composition.

The kit of the present invention may further include one or more containers, including a compartment carrier means used to store samples and containers which contain PCR reaction buffers and DNA polymerases. The carrier means is suitable for containing one or more containers, such as bottles and tubes, and each container includes an independent component used in the method of the present invention. Preparations in the containers that are necessary may be easily used by those of ordinary skill in the art.

In addition, as a means of improving the sensitivity and specificity of prediction of the risk of developing ankylosing spondylitis, the kit and composition of the present invention may further include any one or more primer sets selected from the group consisting of a primer set for detecting a single nucleotide polymorphism, wherein the primer set specifically binds to an SNP marker, rs10865331, composed of sequence No. 29; and a primer set for detecting a single nucleotide polymorphism, wherein the primer set specifically binds to an SNP marker, rs27044, composed of sequence No. 30.

Preferred examples will be suggested to aid in understanding of the present invention. Thus, the present invention will be more easily understood with the below examples. However, the scope of the present invention is not limited by the below examples.

Example 1. Investigation of CNVRs Using Array-CGH Analysis 1-1. Subject of the Study, and Statistical Analysis All subjects of the study consisted of Korean.

For analysis of array-comparative genomic hybridization (CGH), 309 AS patients (male: 278 subjects, females: 31 subjects, age: 22.2±8.3) were recruited from HANYANG UNIVERSITY HOSPITAL FOR RHEUMATIC DISEASES, and the patients were used as a group for discovering copy number variation related to the risk of developing AS. For comparative analysis, a normal control group, consisting of 309 subjects (male: 214 subjects, female: 95 subjects, age: 35.3±13.6), was also recruited from the same hospital. The patients were diagnosed with AS on the basis of 1984 Modified New York Criteria. The study was performed under approval of an institutional review board (CUMC11U199) and carried out with a written consent. In a discovery step, characteristics for the subjects of the study are shown in Table 1 below.

TABLE 1

| | Discovery set | |
|---|---|---|
| Parameter | AS patients (N = 309) | AS controls (N = 309) |
| Age | | |
| Average | 22.2 ± 8.3 | 35.5 ± 13.6 |
| Median | 21 (6-58) | 30 (20-80) |
| Gender | | |
| Male | 278 (90.0%) | 214 (69.3%) |
| Female | 31 (10.0%) | 95 (30.7%) |
| HLA-B27 | | |
| Positive | 300 (97.1%) | 20 (6.5%) |
| Negative | 9 (2.9%) | 289 (93.5%) |
| N/A | — | — |

Statistical analysis was performed using STATA software (version 10.0; Stata Corporation, College Station, Tex.) and SPSS for windows (version 11.5; SPSS, Chicago, Ill.). If a p-value was less than or equal to 0.05, it was considered to be significant.

1-2. Experimental Methods

Whole-genome array-CGH was performed using AGILENT 180K SUREPRINT G3 HUMAN CNV MICROARRAY. The array was carried out to screen DNA copy number variation regions classified by the data of genetic variation and a 1000 genome project. Genomic DNAs isolated from patients and a control group were labeled with Cy5-dCTP (PerkinElmer, Waltham, Mass.), and a reference DNA, NA1085 DNA, was labeled with Cy3-dCTP (PerkinElmer, Waltham, Mass.). The labeled DNAs were subjected to hybridization reaction on an AGILENT 180K array with a hybridized buffer solution and human Cot-1 DNA (Hyb-Masker, ConnectaGen, Seoul, Korea), and then the array slide was incubated at 65° C. for 24 hours, followed by washing and scanning. The scanned image was analyzed by FEATURE EXTRACTION SOFTWARE (Agilent Technologies).

Probe mapping was performed using UCSC GENOME BROWSER (Human NCBI36/hg18). The quality of the data was evaluated by a CGH-QCTM-Sep09 QC metric set. All of the data satisfied the quality evaluation.

1-3. Detection of Copy Number Variations (CNVs)

CNVs were detected, based on log 2 ratios, using ADM2 algorithm in GENOMIC WORKBENCH 7.0 software under a basic setup with slight modifications (the minimum log 2 ratio=3, the minimum number of consecutive probes in a CNV=4).

629,186 CNVs were identified from 618 samples. The median value of CNVs numbers identified in an individual genome was 999 (a range of 488-1515), and the middle size of CNVs was 2.0 Kb (101 bp~5.9 Mbp). The general characteristics of identified CNVs are shown in Table 2 below.

TABLE 2

| Parameters | Case (n = 309) | Control (n = 309) | Total (n = 618) |
|---|---|---|---|
| Total number of CNVs | 306,471 | 312,715 | 619,186 |
| Avg. CNVs per sample (Median) | 991.8 (952) | 1012 (1032) | 1001.9 (999) |
| Gain | 620.1 (574) | 594.2 (607) | 607.1 (594) |
| Loss | 371.8 (366) | 417.8 (414) | 394.8 (388) |
| Avg. of Size (kb) (Median) | 44.9 (1.9) | 52.2 (2.2) | 48.6 (2.0) |
| Ratio (Gain/Loss) | 1.7 | 1.4 | 1.5 |

1-4. Investigation of Copy Number Variation Regions (CNVRs) Related to the Risk of Developing AS After CNV extraction, by means of CNVRuler software, CNV regions (CNVRs) were identified through combining overlapping regions between CNVs obtained from 618 subjects.

Total 3,706 CNVRs were identified, and 1,357 CNVRs among total CNVRs, showing the frequency to be 5% or more, were analyzed to find a correlation between the risk of developing AS and CNVRs. The correlation analysis was performed through logistic regression analysis, whereby the possible changes of experimental results depending on age and gender could be excluded. A false discovery rate (FDR) method was used to resolve the problems of multiple comparisons. In the study, CNVRs with P<0.05 and FDR<0.2 were considered to be significant.

Through the step of discovering CNVRs related to the risk of developing AS, 227 CNVRs among 1,357 CNVRs were verified to have a significant correlation with the onset of AS, satisfying the standard, i.e., P<0.05 and FDR <0.2.

Example 2. Validation of CNVRs Related to the Risk of Developing AS Using Genomic qPCR Based on the results of observing the signal intensities of array-CGH for 227 CNVRs related to the risk of developing AS discovered in Example 1, a quantitative PCR (qPCR) validation was prepared for 79 CNVRs exhibiting relatively distinct signal intensities. As the first step of a qPCR validation, a primer for qPCR, corresponding to each CNVR locus, was designed. Primer sets for 57 loci among 79 loci met the standard of the research team, i.e., $r^2=0.99$ and amplification efficiency: 90 to 110%, and thus the 57 loci were subjected to a qPCR validation, wherein qPCR was performed on the randomly selected 22 samples of a discovery group.

Most reliable 10 chromosome regions, in which the identity of 80% or more between array-CGH and qPCR results was consistently observed, were selected for performing an independent duplication, and the selected 10 chromosome regions are shown in Table 3 below.

TABLE 3

| CNVR | | | Array-CGH Discovery (309 cases vs 309 controls) | | |
|---|---|---|---|---|---|
| Location | Type | Genes | P | FDR | OR(95% CI) |
| 1p34.2 | Loss | BMP8A | $4.6 \times 10^{-10}$ | $1.3 \times 10^{-8}$ | 0.27 (0.18-0.41) |
| 1q32.2 | Loss | HHAT | 0.004 | 0.034 | 1.75 (1.19-2.57) |
| 2q31.2 | Loss | PRKRA | 0.015 | 0.105 | 1.62 (1.10-2.39) |
| 6p24.3 | Loss | BMP6 | $2.6 \times 10^{-8}$ | $3.9 \times 10^{-5}$ | 0.25 (0.14-0.45) |
| 6p21.3 | Loss | HLA-DPB1 | $3.6 \times 10^{-8}$ | $7.9 \times 10^{-7}$ | 2.97 (2.02-4.37) |
| 11q22.1 | Loss | CNTN5 | $1.9 \times 10^{-8}$ | $219 \times 10^{-5}$ | 0.39 (0.27-0.58) |
| 13q13.1 | Loss | EEF1DP3 | 0.019 | 0.126 | 1.59 (1.08-2.36) |
| 14q24.2 | Loss | RGS6 | 0.015 | 0.102 | 0.35 (0.15-0.81) |
| 16p13.3 | Loss | — | $1.7 \times 10^{-6}$ | $2.7 \times 10^{-5}$ | 5.37 (2.70-10.68) |
| 22q11.1 | Gain | IL17RA | $8.7 \times 10^{-31}$ | $1.5 \times 10^{-28}$ | 0.06 (0.04-010) |

Among 10 CNVRs validated by qPCR, 9 CNVRs were of the deletion form and 1 CNVR was of the gain form. Subjects having CNVRs corresponding to 1q32.2 (HHAT), 2q31.2 (PRKRA), 6p21.32 (HLA-DPB1), 13q13.1 (EEF1DP3), and 16p13.3 regions had the significantly higher onset rates of AS compared to a control group, whereas subjects having CNVRs corresponding to 1p34.2 (BMP8A), 6p24.3 (BMP6), 11q22.1 (CNTN5), 14q24.2 (RGS6), and 22q11.1 (IL17RA) regions had lower onset rates of AS compared to the control group. Array-CGH profile and the result of a qPCR validation in a CNVR corresponding to the 1q32.2 region are shown in FIGS. 1 to 3.

Figure 2:
FIG. 2 illustrates the ratios of signal strengths of the 1q32.2 region, in which the ratios are represented by colors, as the result of array-CGH experiments.
Figure 3:
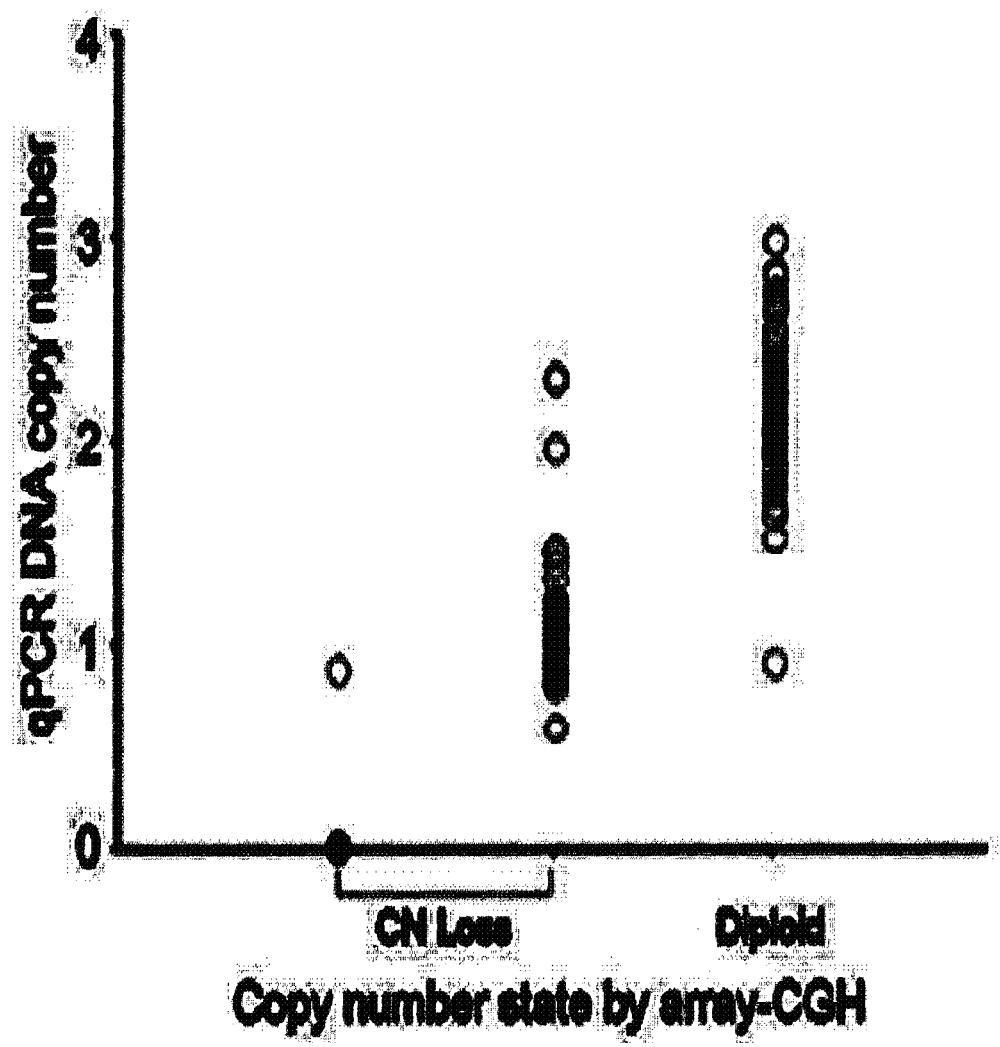
FIG. 3 illustrates the result of genomic quantitative PCR that validated DNA copy number variation in the 1q32.2 region.

As illustrated in FIGS. 1 to 3, on the basis of the signal intensity ratio of a 1q32.2 region, which was represented by a log 2 ratio value (a negative value) and color (green), it was verified that the 1q32.2 region was deleted, and the reduced copy number of the region was confirmed by qPCR.

Example 3. An Independent Replication of CNVRs Related to the Risk of Developing AS Using Genomic qPCR

3-1. A Subject of the Study, and Statistical Analysis

All subjects of the study consisted of Korean.

An independent replication consisting of two steps was performed on the discovered 10 CNVRs related to the risk of developing AS. The first step of the independent replication targeted at 491 AS patients and 671 subjects of a normal control group, and the second step of the independent replication targeted 134 AS patients and 274 subjects of a normal control group. All subjects of the first- and second-step independent replication groups were recruited from HANYANG UNIVERSITY HOSPITAL FOR RHEUMATIC DISEASES and EULJI UNIVERSITY HOSPITAL, and qPCR was performed on the interested loci. The study was performed under approval of an institutional review board (CUMC11U199) and carried out with a written consent. In a replication step, characteristics for the subjects of the study are shown in Table 4 below.

TABLE 4

| | 1st Replication set | | 2nd Replication set | |
|---|---|---|---|---|
| Parameter | AS patients (N = 491) | AS controls (N = 617) | AS patients (N = 134) | AS controls (N = 274) |
| Age | | | | |
| Average | 24.3 ± 8.5 | 34.1 ± 10.7 | 24.6 ± 8.6 | 14.2 ± 9.0 |
| Median | 23 (5-62) | 31 (20-70) | 23 (10-65) | 10 (10-58) |
| Gender | | | | |
| Male | 443 (90.2%) | 535 (86.7%) | 124 (92.5%) | 233 (85.0%) |
| Female | 48 (9.8%) | 82 (13.3%) | 10 (7.5%) | 41 (15.0%) |
| HLA-B27 | | | | |
| Positive | 475 (96.7%) | 34 (5.5%) | 131 (97.8%) | 16 (5.8%) |
| Negative | 16 (3.3%) | 578 (93.7%) | 3 (2.2%) | 258 (94.2%) |
| N/A | — | 5 (0.8%) | — | — |

Statistical analysis was performed using STATA software (version 10.0; Stata Corporation, College Station, Tex.) and SPSS for windows (version 11.5; SPSS, Chicago, Ill.). If a p-value was less than or equal to 0.05, it was considered to be significant.

3-2. The Preparation of Primer Sets for Performing Genomic qPCR

A primer set for amplification, which is specific to each locus, was designed to perform genomic quantitative PCR (qPCR) on the discovered 10 CNVRs related to the risk of developing AS, and then, in the discovery step, it was intended that an independent duplication was performed on CNVRs highly related to AS, using the primer set.

The information of primers used in the experiments of the present invention is shown in Table 5 below.

TABLE 5

| CNVR location | Start (bp) | End (bp) | Amplicon size (bp) | forward | Reverse | Coefficient | efficiency |
|---|---|---|---|---|---|---|---|
| 1p34.2 | 39.764.318 | 39.764.437 | 120 | GAGTCAGCAC AGAAGTCCTA TC (SEQ ID NO: 1) | CCCTTCTCCT CACACCTAAA C (SEQ ID NO: 2) | 0.996 | 102% |
| 1q32.2 | 208,789,321 | 208,789498 | 178 | ACCTGTGAAG GATGGATTG GCAGA (SEQ ID NO: 3) | TGGCCTTTGA GCACTGACTG ACTA (SEQ ID NO: 4) | 0.991 | 107% |
| 2q31.2 | 179,004,645 | 179,004,759 | 115 | TAAAGGCCTG TTAGTGCTGT CCCT (SEQ ID NO: 5) | GCGACAGTCT TTCTTACTGG TGCT (SEQ ID NO: 6) | 0.996 | 92% |
| 6p21.32 | 33.162.149 | 33.162.313 | 165 | ATTGCTTGGC TCCATTGCTG AAGG (SEQ ID NO: 7) | TTTCAGTGAG CTCAGGAACC CTGT (SEQ ID NO: 8) | 0.997 | 92% |
| 11q22.1 | 99.195.496 | 99.195.605 | 110 | TCTCTTCCTG GTCTCTCCAC TTCA (SEQ ID NO: 9) | AATGAAGGGC TGCTGTATCG TGGT (SEQ ID NO: 10) | 0.998 | 99% |
| 13q13.1 | 31.431.435 | 31.431.520 | 86 | CCAAGCCTGG ACATCAATGA GCTA (SEQ ID NO: 11) | ATGCCATAGG CTTTCCAAGA TGCC (SEQ ID NO: 12) | 0.996 | 100% |
| 14q24.2 | 71.877.208 | 71.877.298 | 91 | TGTGAAAGGC TCTCTCATTG CCCT (SEQ ID NO: 13) | ATCTGCTCTG CATGGGACAG AAGT (SEQ ID NO: 14) | 0.995 | 103% |
| 16p.13.3 | 2.638.642 | 2.638.771 | 112 | TCAACATCCA GCATCCCACA CTCA (SEQ ID NO: 15) | ACTTGATGGG AGGAGAAACC CACA (SEQ ID NO: 16) | 0.996 | 96% |
| 22q11.1 | 15.968.551 | 15.968.662 | 112 | CCCTGTGAGC TGGTTTCTA TT (SEQ ID NO: 17) | TGACCGGTGT ATTTGGTGTC (SEQ ID NO: 18) | 0.995 | 101% |
| 6p24.3 | 7.726.951 | 7.727.119 | 169 | TGAGTGAAG TTCCCTGAAC GAGCA (SEQ ID NO: 19) | ATATGGCCTG AAAGACCTCG CACT (SEQ ID NO: 20) | 0.996 | 94% |

Quantitative PCR was performed using ViiA7 system (Life Technologies, Carlsbad, Calif.), and a NA10851 sample was used as a calibrator. Copy number variation of each subject was defined by $2^{-ct}$, wherein Ct refers to a difference of threshold cycles for values obtained from a reference gene (HS6ST3) and a calibrator DNA (an individual/a calibrator) in a sample to be identified, and the value of a ratio was rounded to the nearest integer. A criterion for quality assessment of a control group in qPCR was defined as the case of a Ct value less than 0.3.

3-3. The independent replication results of CNVRs related to AS In an independent replication group, the results of qPCR performed on 10 CNVRs in two steps are shown in Table 6.

TABLE 6

| CNVR | | | 1st Replication by qPCR* (491 cases vs 617 controls) | | | 2nd Replication by qPCR* (134 cases vs 274 controls) | | | Combined** (934 cases vs 1200 controls) | | |
|---|---|---|---|---|---|---|---|---|---|---|---|
| Location | Type | Genes | P | FDR§ | OR (95% CI) | P | FDR§ | OR (95% CI) | P | FDR§ | OR (95% CI) |
| 1p34.2 | Loss | BMP8A | 0.002 | 0.004 | 0.25 (0.10-0.61) | 0.827 | 0.827 | 0.93(0.48-1.81) | $6.3 \times 10^{-12}$ | $2.1 \times 10^{-11}$ | 0.38 (0.29-0.50) |
| 1q32.2 | Loss | HHAT | 0.021 | 0.023 | 1.38 (1.05-1.81) | 0.047 | 0.125 | 1.67(1.01-2.77) | $1.3 \times 10^{-5}$ | $1.3 \times 10^{-6}$ | 1.56 (1.30-1.87) |
| 2q31.2 | Loss | PRKRA | 0.002 | 0.004 | 1.61 (1.19-2.18) | $4.7 \times 10^{-5}$ | $4.7 \times 10^{-4}$ | 3.30(1.86-5.87) | $9.9 \times 10^{-12}$ | $9.9 \times 10^{-11}$ | 1.96 (1.62-2.39) |
| 6p24.3 | Loss | BMP6 | 0.972 | 0.972 | 1.01 (0.53-1.92) | 0.466 | 0.517 | 0.63(0.18-2.18) | 0.009 | 0.009 | 0.63 (0.44-0.89) |
| 6p21.32 | Loss | HLA-DPB1 | $2.1 \times 10^{-4}$ | 0.001 | 1.94 (1.37-2.76) | 0.050 | 0.125 | 1.86(1.00-3.47) | $3.2 \times 10^{-10}$ | $6.4 \times 10^{-10}$ | 1.92 (1.57-2.35) |

TABLE 6-continued

| CNVR | | | 1st Replication by qPCR* (491 cases vs 617 controls) | | | 2nd Replication by qPCR* (134 cases vs 274 controls) | | | Combined** (934 cases vs 1200 controls) | | |
|---|---|---|---|---|---|---|---|---|---|---|---|
| Location | Type | Genes | P | FDR§ | OR (95% CI) | P | FDR§ | OR (95% CI) | P | FDR§ | OR (95% CI) |
| 11q22.1 | Loss | CNTN5 | $9.8 \times 10^{-6}$ | $4.9 \times 10^{-5}$ | 0.51 (0.37-0.68) | 0.121 | 0.201 | 0.66(0.39-1.12) | $7.4 \times 10^{-14}$ | $3.7 \times 10^{-13}$ | 0.48 (0.39-0.58) |
| 13q13.1 | Loss | EEF1DP3 | 0.001 | 0.002 | 1.65 (1.23-2.20) | 0.293 | 0.367 | 1.33(0.78-2.29) | $5.4 \times 10^{-7}$ | $7.7 \times 10^{-7}$ | 1.62 (1.34-1.96) |
| 14q24.2 | Loss | RGS6 | 0.009 | 0.013 | 0.49 (0.29-0.84) | 0.188 | 0.268 | 0.56(0.23-1.33) | $2.9 \times 10^{-5}$ | $3.2 \times 10^{-6}$ | 0.42 (0.29-0.60) |
| 16p13.3 | Loss | — | 0.012 | 0.015 | 1.86 (1.15-3.02) | 0.002 | 0.012 | 2.56(1.40-4.69) | $3.4 \times 10^{-7}$ | $5.6 \times 10^{-7}$ | 2.11 (1.58-2.80) |
| 22q11.1 | Gain | IL17RA | $1.3 \times 10^{-9}$ | $1.3 \times 10^{8}$ | 0.38 (0.28-0.52) | 0.075 | 0.150 | 0.38(0.13-1.10) | $5.5 \times 10^{35}$ | $5.5 \times 10^{-34}$ | 0.24 (0.19-0.30) |

As the result of an independent replication of the first step (491 subjects as an experimental group and 617 subjects as a control group), 9 of 10 CNVRs consistently exhibited significant results, and also the direction of odds ratios exhibited a result identical with the discovery step (five risk-increasing and four protective CNVRs). On the other hand, in 1 CNVR, 6p24.3, the significance of a discovery group was not identified in an independent replication group.

In an independent replication of the second step (134 subjects as an experimental group and 274 subjects as a control group), 4 CNVRs consistently exhibited significant results, and also the direction of odds ratios exhibited a result identical with the discovery step and the independent replication of the first step (see Table 3). In other words, CNVRs corresponding to 1q32.2, 2q31.2, 6p21.32, and 16p13.3 regions consistently exhibited significance in all 3 step sets.

In addition, besides NA10851, a reference DNA of qPCR, analysis using a subject for whom the CNVR locus is 2n, as another reference of qPCR, was also performed in the independent replication of the present invention.

Figure 4:
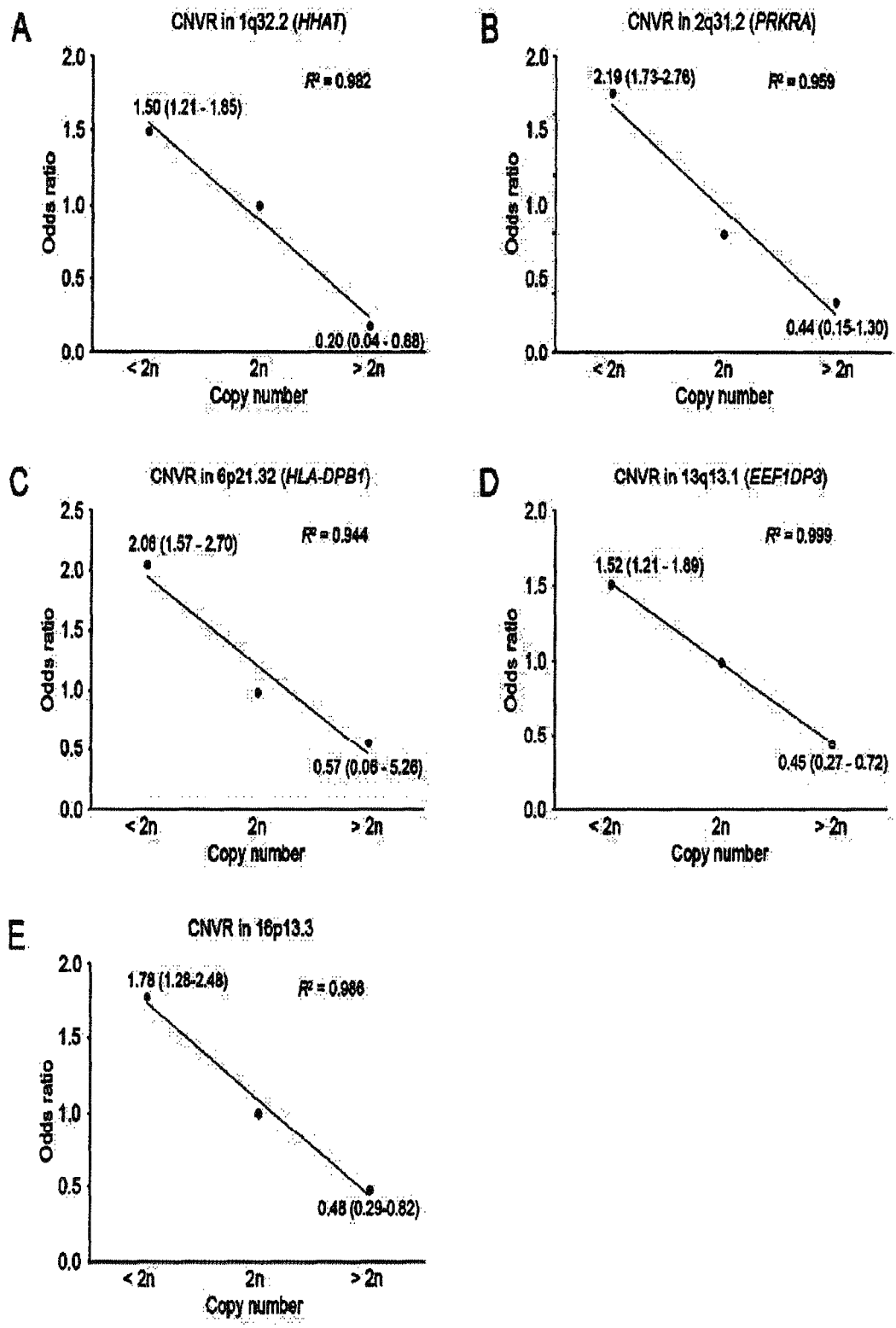
FIG. 4 illustrates odds ratios for the onset rates of ankylosing spondylitis (AS) according to copy number (<2n, 2n, >2n) variation of 1q32.2 (A), 2q31.2 (B), 6p21.32 (C), 13q13.1 (D), and 16q13.3 (E) CNV regions (CNVRs).

As illustrated in FIG. 4, subjects having copy number variation due to deletion in the discovered CNVRs corresponding to 1q32.2 (A), 2q31.2 (B), 6p21.32 (C), 13q13.1 (D), and 16p13.3 (E) regions, which were identified to increase the onset rate of AS in the discovery step, exhibited higher onset rates of AS compared to subjects having 2n. As copy number decreased, odds ratios increased, and the odds ratios exhibited a result which significantly depended on the degree of copy number decrease ($r^2$=0.944 to 0.999).

Subjects having copy number variation in the discovered CNVRs corresponding to 1p34.2, 11q22.1, 14q24.2, and 22q11.1 regions, which were identified to decrease the onset rate of AS in the discovery step, exhibited lower onset rates of AS compared to subjects having 2n. However, odds ratios did not exhibit a result which significantly depended on copy number.

According to combined analysis results which combined all of the results of the discovery group and the first- and second-step independent replication groups, all of the above 9 types of CNVRs (CNVRs, which have a high correlation with the onset of AS, including 1q32.2, 2q31.2, 6p21.32, 13q13.1, and 16p13.3; CNVRs, which have a low correlation with the onset of AS, including 1p34.2, 11q22.1, 14q24.2, and 22q11.1) exhibited significance in relation to AS, and all CNVRs exhibited higher significance in the combined analysis results compared to the result of each of the discovery and the first- and second-step independent replications ("Combined" column in Table 6).

Example 4. Identification of the Sizes and Deletion Boundaries of CNVRs Using Deletion-Typing PCR 4-1. Experimental Methods 8 deletion-type CNVRs of the validated 9 CNVRs were subjected to deletion-typing PCR to identify the accurate sizes and boundaries of deletions. According to primer design for deletion-typing as the first step of deletion-typing PCR, 3 CNVRs, including 1q32.2, 13q13.1, and 14q24.2, of the 8 CNVRs were verified to be useable for identifying deletions using the PCR method. After that, deletion-typing PCR was performed using primer sets for the 3 CNVRs. The amplicons of deleted alleles were subjected to sequencing analysis using PCR-direct sequencing.

The primer sets for detecting deletion regions were designed within the flanking sequences of estimated deletion regions. An experimental strategy is illustrated in (A) of FIG. 5, and the information of the primers is shown in Table 7 below.

TABLE 7

| Target Region | Forward primer (5'-3') | Reverse Primer (3'-5') |
|---|---|---|
| 1q32.2 | AGTGCTTTAAGGGTGCGTTGTTGG (SEQ ID NO: 21) | ACTTTCACAGCACCTCCACAGACT (SEQ ID NO: 22) |
| 13q13.1 | AGGCATTCCCACATGCACAAACAG (SEQ ID NO: 23) | AGTTCACTGCAGTCACCCTTGGAA (SEQ ID NO: 24) |
| 14q24.2 | AACCCACAAGCAGAGGAAGGAGAA (SEQ ID NO: 25) | ATGTGTGTGGTGCTGACATTGCTG (SEQ ID NO: 26) |

Figure 5:
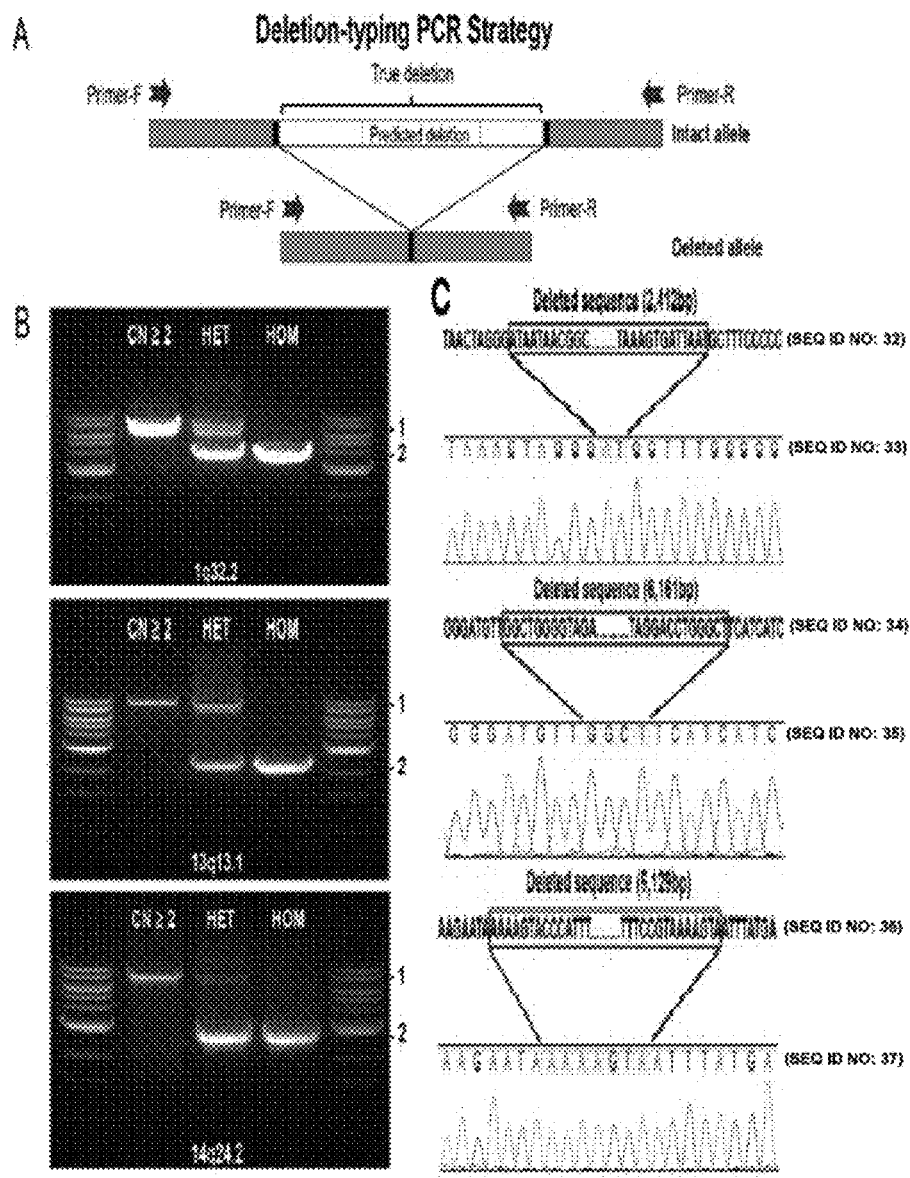
FIG. 5 illustrates (A) a diagram for performing deletion typing PCR, (B) the electrophoretic gel images of deletion typing PCR results, and (C) sequencing results showing DNA sequences adjacent to the deletion regions.

To summarize the experimental strategy of performing PCR on a region including a predicted deletion illustrated in (A) of FIG. 5, in the absence of a deletion, a PCR amplicon with a predicted size is observed, whereas, in the presence of a deletion, a PCR amplicon has a length corresponding to a sequence region excluding the deleted region, thus exhibiting a shortened size. A box within a white region in (A) of FIG. 5 represents the predicted deletion region, and the white region, including the box, represents a true deletion region. And blue arrows and back vertical bars represent a primer set for detecting a deletion and microhomology sequences, respectively.

4-2. Identification of the Sizes and Deletion Boundaries of CNVRs

As illustrated in (B) and (C) of FIG. 5, in a 1q32.2 region, the length of a deleted region was identified to be 2.4 Kb or less using deletion typing PCR, which was almost identical to the deletion length, i.e., 2,412 bp, identified by sequencing, and the mechanism of CNVRs was non-homologous end joining (NHEJ) by 2 bp microhomology (AT).

In a 13q13.1 region, the length of a deleted region was identified to be 6.2 Kb or less using deletion typing PCR, which was almost identical to the deletion length, i.e., 6.161 bp, identified by sequencing, and the mechanism of CNVRs was NHEJ by 4 bp microhomology (GGCT).

In a 14q24.2 region, the length of a deleted region was identified to be 5.1 Kb or less using deletion typing PCR, which was almost identical to the deletion length, i.e., 5.129 bp, identified by sequencing, and the mechanism of CNVRs was NHEJ by 7 bp microhomology (AAAAGTA). In (B) of FIG. 5, "HOM" and "HET" represent homozygous deletion and heterozygous deletion, respectively. In (C) of FIG. 5, yellow bars and red boxes represent microhomology sequences and deleted sequences, respectively.

Example 5. The Onset Rates of AS According to Deletion, and the Comparison of the Onset Rates of AS Between Homozygous Deletion and Heterozygous Deletion Deletion-typing PCR and PCR-direct sequencing were performed for 3 CNVRs, including 1q32.2, 13q13.1 and 14q24.2, of total 849 cases in AS patients and 922 cases in a normal control group, and the results are shown in Table 8 below.

The onset rates of AS were compared between subjects verified to have CNVRs corresponding to 1q32.2, 13q13.1, and 14q24.2 regions using deletion-typing PCR and subjects having 2n, as a reference. And the onset rates of AS between homozygous deletion and heterozygous deletion were compared in subjects verified to have CNVRs corresponding to 1q32.2, 13q13.1, and 14q24.2 regions.

As illustrated in FIG. 6, subjects having a CNVR, which a 1q32.2 region was deleted, exhibited higher onset rates of AS compared to subjects with 2n (OR=1.43, 95% CI: 1.17 to 1.75, P=$4.9 \times 10^{-4}$), and the cases of homozygous deletion exhibited higher onset rates of AS compared to those of heterozygous deletion (OR=2.21, P=$3.1 \times 10^{-5}$ in HOM versus OR=1.29, P=0.020 in HET).

Subjects having a CNVR, which a 13q13.1 region was deleted, exhibited higher onset rates of AS compared to subjects with 2n (OR=1.26, 95% CI: 1.03 to 1.54, P=0.023), and the cases of homozygous deletion exhibited higher onset rates of AS compared to those of heterozygous deletion (OR=1.59, P=$9.3 \times 10^{-4}$ in HOM versus OR=1.09, P=0.473 in HET).

Subjects having a CNVR, which a 14q24.2 region was deleted, exhibited lower onset rates of AS compared to subjects with 2n (OR=0.62, 95% CI: 0.41 to 0.95, P=0.027), and odds ratios were not related with dosage.

Example 6. Identification of a Correlation Between Simultaneous Copy Number Variation of CNVRs and the Onset Rate of AS The onset rates of AS were compared between subjects, who had one or more copy number variation simultaneously occurring in CNVRs responsible for increasing the onset of AS or subjects, who had one or more copy number variation simultaneously occurring in CNVRs responsible for decreasing the onset of AS and subjects with no deletion on CNVRs. With regard to the effect of copy number variation on increasing the risk of developing AS, 5 types of CNVRs, including 1q32.2, 2q31.2, 6p21.32, 13q13.1, and 16p13.3, were investigated to reveal a correlation between the risk of developing AS and the existence of copy number variation, whereas, with regard to the effect of copy number variation on decreasing the risk of developing AS, 3 types of CNVRs, including 1p34.2, 11q22.1, and 14q24.2, were investigated to reveal a correlation between the risk of developing AS and the existence of copy number variation.

As shown in FIG. 7 and Table 9, the onset rates of AS in subjects with four or more copy number variation in CNVRs responsible for increasing the onset of AS were approximately 18 times higher than those in subjects with no copy number variation in CNVRs (OR=17.98, 95% CI: 6.02 to 53.70, P=$2.3 \times 10^{-7}$). As the number of CNVRs responsible for increasing the onset of AS increased, odds ratios increased ($r^2$=0.999).

TABLE 8

| CNVR Location | Start (bp) | End (bp) | Length (bp) | Type | Genes | Mechanism | Microhomology | Deletion-typing PCR (849 cases vs 922 controls) | | |
|---|---|---|---|---|---|---|---|---|---|---|
| | | | | | | | | P | FDR§ | OR (95% CI) |
| 1q32.2 | 208,789,092 | 208,791,503 | 2,4112 | Loss | HHAT | NHEJ | AT | $4.9 \times 10^{-4}$ | 0.001 | 1.43(1.17-1.75) |
| 13q13.1 | 31,430,645 | 31,436,805 | 6,161 | Loss | EEFIDP3 | NHEJ | GGCT | 0.0213 | 0.027 | 1.26(1.03-1.54) |
| 14q24.2 | 71,875,556 | 71,880,684 | 5,129 | Loss | RGS6 | NHEJ | AAAAGTA | 0.027 | 0.027 | 0.62(0.41-0.95) |

TABLE 9

| Frequency | Case (625) | Control (891) |
|---|---|---|
| 5 loci | 19 (3.0%) | 4 (0.4%) |
| 4 loci | 108 (17.3%) | 83 (9.3%) |
| 3 loci | 229 (36.6%) | 223 (25.0%) |
| 2 loci | 201 (32.2%) | 328 (36.8%) |
| 1 locus | 64 (10.2%) | 210 (23.6%) |
| None in all 5 loci | 4 (0.6%) | 43 (4.8%) |

In addition, as shown in FIG. 8 and Table 10, the onset rates of AS in subjects with two or more copy number variation in CNVRs responsible for decreasing the onset of AS were 5.2 times lower than those in subjects with no copy number variation in CNVRs (OR=0.19, 95% CI: 0.12 to 0.32, P=4.0×10$^{-10}$). As the number of CNVRs responsible for decreasing the onset of AS increased, odds ratios decreased ($r^2$=0.9849).

TABLE 10

| Type | Case (625) | Control (891) |
| --- | --- | --- |
| 3 loci | 3 (0.5%) | 9 (1.0%) |
| 2 loci | 17 (2.7%) | 87 (9.8%) |
| 1 locus | 213 (34.1%) | 323 (36.2%) |
| None in all 3 loci | 392 (62.7%) | 472 (53.0%) |

The results indicate that the results of copy number variation for specific CNVRs may be used to more precisely predict whether the onset of ankylosing spondylitis occurs.

Example 7. Identification of a Correlation Between Single Nucleotide Polymorphism (SNP) and the Onset Rate of AS 7-1. Experimental Methods Single nucleotide polymorphism (SNP) analysis was performed on AS patients, who had been subjected to a copy number variation test for 5 CNVRs responsible for increasing the onset rate of AS, and, as a control group, 701 subjects (339 patients and 362 subjects of a control group), whose DNA samples were available.

The 5 types of SNP markers were selected, including rs27037, rs27434, rs10865331, rs27044, and rs30187, which had been known to increase the onset rate of ankylosing spondylitis in Korean people. qPCR reaction was performed using primers and probes specific to the 5 types of SNP markers, and genotype of each SNP marker was analyzed on the basis of fluorescence signal generated from each cycle of PCR reaction. The primers and probes specific to the SNP markers used in the analysis were purchased from Life Technologies Corporation, and the information of the markers used is shown in Table 11 below.

TABLE 11

| SNP marker | Assay ID | Context Sequence |
| --- | --- | --- |
| rs27037 | C___794737_30 | ATTATTATTATTACAATTGTTAGGG[G/T]TCT TTTTTCTTTTAGAAATTCAAAG (SED ID NO: 27) |
| rs27434 | C___794791_10 | AGTGTGAATGAGCTTATACCTGGTG[A/G]GCC AGTTCATGGGCCACAGTCATTG (SED ID NO: 28) |
| rs10865331 | C___440025_20 | ACTGACTTTGGTGCCGTATCTACCA[A/G]GTG GTCAAGCTGATGCCATTGXAAG (SED ID NO: 29) |
| rs27044 | C___3056870_10 | TGCACACAGGCGAGGAGTAGTAGTT[C/G]ACT CCGCAGCATTCGCTCTGAGACT (SED ID NO: 30) |
| rs30187 | C___3056885_10 | TGTGATGGTTATTAGGGGAAAACCC[C/T]TCT GCAGTGTCCAAGTGTTCATCAT (SED ID NO: 31) |

7-2. Independent Replication of Single Nucleotide Polymorphism (SNP) Related to AS According to the result of genotyping each of the 5 types of SNP markers, the risk of developing ankylosing spondylitis was evaluated, and the genotyping results are shown in Table 12 below.

TABLE 12

| | Dominant | OR | Lower_CI | Upper_CI |
| --- | --- | --- | --- | --- |
| rs27037 | 0.0676 | 1.25 | 0.98 | 1.59 |
| rs27434 | 0.0168 | 1.44 | 1.07 | 1.94 |
| rs10865331 | 0.0059 | 1.41 | 1.10 | 1.80 |
| rs27044 | 0.0048 | 1.65 | 1.16 | 2.34 |
| rs30187 | 0.0299 | 1.38 | 1.03 | 1.84 |

As shown in Table 12, the genotypes of 4 types of SNPs, including rs27434, rs10865331, rs27044, and rs30187, among the 5 types of SNPs used in Example 7 of the present invention exhibited a significant correlation with the onset rate of AS.

Example 8. Verification of the Accuracy of Predicting the Onset Rate of AS Using CNVRs and Single Nucleotide Polymorphism (SNP)

Based on the results from the 5 types of CNVRs related to AS identified in Example 6 and the 5 types of SNPs related to AS identified in Example 7, receiver-operating characteristic (ROC) curve analysis was performed. A prediction model for the risk of developing AS, which has superior sensitivity and specificity, was intended to be identified through the analysis in Example 8.

As shown in Table 13, an ROC analysis was performed on a set using 5 types of CNVRs, a set using all 5 types of CNVRs and 5 types of SNPs, a set using 5 types of CNVRs and 4 types of SNPs (rs27434, rs10865331, rs27044, rs30187), and a set using 5 types of CNVRs and 2 types of SNPs (rs10865331, rs27044) satisfying P<0.01.

TABLE 13

| Set | Contents | Description |
| --- | --- | --- |
| 5 AS risk CNVRs | 5 AS risk CNVRs | |
| ROC_Set1 | 5 AS risk CNVRs + 5 AS risk SNPs | |
| ROC_Set2 | 5 AS risk CNVRs + 4 AS risk SNPs | (P < 0.05, SNPs) |
| ROC_Set3 | 5 AS tisk CNVRs + 2 AS risk SNPs | (P < 0.01, SNPs) |

As shown in Table 14 and FIGS. 9 to 12, a case of using CNVRs together with SNPs (Area value; 0.652, 0.667, 0.684) exhibited a superior prediction result compared to a case of using CNVRs alone (Area value; 0.632). Particularly, a case (ROC_Set3) of using established 5 types of CNVRs together with 2 types of SNPs which were verified to be P<0.01 in an independent replication result exhibited the best result.

TABLE 14

Area Under the Curve

| Test Result Variable(s) | Area | Std. Erros | Asymptotic Sig. b | Asymptotic 95% Confidence Interval | |
|---|---|---|---|---|---|
| | | | | Lower Bound | Upper Bound |
| ROC_set1 | .652 | .021 | .000 | .610 | .694 |
| ROC_set2 | .667 | .021 | .000 | .626 | .709 |
| ROC_set3 | .684 | .020 | .000 | .645 | .723 |
| 5 AS risk CNVRs | .632 | .017 | .000 | .600 | .665 |

In addition, as illustrated in FIG. 13, when ROC curve analysis was performed on HLA-B27 positive subjects alone, including 501 AS patients and 30 subjects as a control group, for the set3 marker combination (5 types of CNVRs+2 types of SNPs) which had shown the best result, the obtained result (Area=0.707) was better than a result (Area=0.684) from the entire subjects of the analysis.

When compared to a method of prediction on the basis of copy number variation of CNVRs alone, a method of prediction combining the results obtained from copy number variation of CNVRs and single nucleotide polymorphism may provide a more accurate prediction of the onset of ankylosing spondylitis.

The aforementioned description of the present invention is provided by way of examples and those skilled in the art will understand that the present invention can be easily changed or modified into other specified forms without change or modification of the technical spirit or the essential characteristics of the present invention. Therefore, it should be understood that the aforementioned examples are only provided as examples and not provided to limit the present invention.

INDUSTRIAL APPLICABILITY

The present invention relates to a method of predicting the risk of developing ankylosing spondylitis using DNA copy number variation. In contrast to an existing method of prediction using HLA-B27 antigen gene, the method of the present invention may enable a more precise prediction of onset of ankylosing spondylitis using results obtained from DNA copy number variation and single nucleotide polymorphism (SNP) analyses for a specific region. Accordingly, the method or composition of the present invention may be used in applied research based on the same as well as early prevention and diagnosis of ankylosing spondylitis.

The invention claimed is:

1. A method of predicting a risk of developing ankylosing spondylitis, the method comprising:
   (a) a step of performing polymerase chain reaction (PCR) on genomic DNA samples isolated from a human subject, wherein the genomic DNA samples have been independently treated with the following primer sets for detecting DNA copy number variation:
      a primer set for detecting DNA copy number variation on chromosome 1q32.2, wherein the primer set is composed of SEQ ID NO. 3 as a forward primer and SEQ ID NO. 4 as a reverse primer,
      a primer set for detecting DNA copy number variation on chromosome 13q13.1, wherein the primer set is composed of SEQ ID NO. 11 as a forward primer and SEQ ID NO. 12 as a reverse primer, and
      a primer set for detecting DNA copy number variation on chromosome 16p13.3, wherein the primer set is composed of SEQ ID NO. 15 as a forward primer and SEQ ID NO. 16 as a reverse primer;
   (b) a step of generating each PCR product;
   (c) a step of performing sequencing of each of the PCR product;
   (d) a step of determining a size in base pair length of the each PCR product by electrophoresis;
   (e) a step of comparing the size of the each PCR product with that of a PCR product of a corresponding wild type chromosome without any deletions; and
   (f) a step of predicting the subject as belonging in a high-risk group for onset of ankylosing spondylitis if the size of the one or more PCR products determined in the step (d) are a deletion type which is shorter than that of the PCR product(s) of the corresponding wild type chromosome(s) without any deletions.

2. The method according to claim 1, wherein the PCR in step (a) is genomic quantitative PCR or deletion-typing PCR.

* * * * *

SEQUENCE LISTING

```
<160> NUMBER OF SEQ ID NOS: 37

<210> SEQ ID NO 1
<211> LENGTH: 22
<212> TYPE: DNA
<213> ORGANISM: Artificial Sequence
<220> FEATURE:
<223> OTHER INFORMATION: 1p34.2 forward primer

<400> SEQUENCE: 1
gagtcagcac agaagtccta tc                                              22

<210> SEQ ID NO 2
<211> LENGTH: 21
<212> TYPE: DNA
<213> ORGANISM: Artificial Sequence
<220> FEATURE:
<223> OTHER INFORMATION: 1p34.2 reverse primer

<400> SEQUENCE: 2
cccttctcct cacacctaaa c                                               21

<210> SEQ ID NO 3
<211> LENGTH: 24
<212> TYPE: DNA
<213> ORGANISM: Artificial Sequence
<220> FEATURE:
<223> OTHER INFORMATION: 1q32.2 forward primer

<400> SEQUENCE: 3
acctgtgaag gatggattgg caga                                            24

<210> SEQ ID NO 4
<211> LENGTH: 24
```

```
<212> TYPE: DNA
<213> ORGANISM: Artificial Sequence
<220> FEATURE:
<223> OTHER INFORMATION: 1q32.2 reverse primer

<400> SEQUENCE: 4
tggcctttga gcactgactg acta                                              24

<210> SEQ ID NO 5
<211> LENGTH: 24
<212> TYPE: DNA
<213> ORGANISM: Artificial Sequence
<220> FEATURE:
<223> OTHER INFORMATION: 2q31.2 forward primer

<400> SEQUENCE: 5
taaaggcctg ttagtgctgt ccct                                              24

<210> SEQ ID NO 6
<211> LENGTH: 24
<212> TYPE: DNA
<213> ORGANISM: Artificial Sequence
<220> FEATURE:
<223> OTHER INFORMATION: 2q31.2 reverse primer

<400> SEQUENCE: 6
gcgacagtct ttcttactgg tgct                                              24

<210> SEQ ID NO 7
<211> LENGTH: 24
<212> TYPE: DNA
<213> ORGANISM: Artificial Sequence
<220> FEATURE:
<223> OTHER INFORMATION: 6p21.32 forward primer

<400> SEQUENCE: 7
attgcttggc tccattgctg aagg                                              24

<210> SEQ ID NO 8
<211> LENGTH: 24
<212> TYPE: DNA
<213> ORGANISM: Artificial Sequence
<220> FEATURE:
<223> OTHER INFORMATION: 6p21.32 reverse primer

<400> SEQUENCE: 8
tttcagtgag ctcaggaacc ctgt                                              24

<210> SEQ ID NO 9
<211> LENGTH: 24
<212> TYPE: DNA
<213> ORGANISM: Artificial Sequence
<220> FEATURE:
<223> OTHER INFORMATION: 11q22.1 forward primer

<400> SEQUENCE: 9
tctcttcctg gtctctccac ttca                                              24

<210> SEQ ID NO 10
<211> LENGTH: 24
<212> TYPE: DNA
<213> ORGANISM: Artificial Sequence
<220> FEATURE:
<223> OTHER INFORMATION: 11q22.1 reverse primer

<400> SEQUENCE: 10
```
aatgaagggc tgctgtatcg tggt                                                  24

<210> SEQ ID NO 11
<211> LENGTH: 24
<212> TYPE: DNA
<213> ORGANISM: Artificial Sequence
<220> FEATURE:
<223> OTHER INFORMATION: 13q13.1 forward primer

<400> SEQUENCE: 11
ccaagcctgg acatcaatga gcta                                                  24

<210> SEQ ID NO 12
<211> LENGTH: 24
<212> TYPE: DNA
<213> ORGANISM: Artificial Sequence
<220> FEATURE:
<223> OTHER INFORMATION: 13q13.1 reverse primer

<400> SEQUENCE: 12
atgccatagg ctttccaaga tgcc                                                  24

<210> SEQ ID NO 13
<211> LENGTH: 24
<212> TYPE: DNA
<213> ORGANISM: Artificial Sequence
<220> FEATURE:
<223> OTHER INFORMATION: 14q24.2 forward primer

<400> SEQUENCE: 13
tgtgaaaggc tctctcattg ccct                                                  24

<210> SEQ ID NO 14
<211> LENGTH: 24
<212> TYPE: DNA
<213> ORGANISM: Artificial Sequence
<220> FEATURE:
<223> OTHER INFORMATION: 14q24.2 reverse primer

<400> SEQUENCE: 14
atctgctctg catgggacag aagt                                                  24

<210> SEQ ID NO 15
<211> LENGTH: 24
<212> TYPE: DNA
<213> ORGANISM: Artificial Sequence
<220> FEATURE:
<223> OTHER INFORMATION: 16p13.3 forward primer

<400> SEQUENCE: 15
tcaacatcca gcatcccaca ctca                                                  24

<210> SEQ ID NO 16
<211> LENGTH: 24
<212> TYPE: DNA
<213> ORGANISM: Artificial Sequence
<220> FEATURE:
<223> OTHER INFORMATION: 16p13.3  reverse primer

<400> SEQUENCE: 16
acttgatggg aggagaaacc caca                                                  24

<210> SEQ ID NO 17
<211> LENGTH: 20
<212> TYPE: DNA
<213> ORGANISM: Artificial Sequence

```
<220> FEATURE:
<223> OTHER INFORMATION: 22q11.1 forward primer

<400> SEQUENCE: 17
ccctgtgagc tggtttctat                                              20

<210> SEQ ID NO 18
<211> LENGTH: 20
<212> TYPE: DNA
<213> ORGANISM: Artificial Sequence
<220> FEATURE:
<223> OTHER INFORMATION: 22q11.1 reverse primer

<400> SEQUENCE: 18
tgaccggtgt atttggtgtc                                              20

<210> SEQ ID NO 19
<211> LENGTH: 24
<212> TYPE: DNA
<213> ORGANISM: Artificial Sequence
<220> FEATURE:
<223> OTHER INFORMATION: 6p24.3  forward primer

<400> SEQUENCE: 19
tgagtgaagt tccctgaacg agca                                         24

<210> SEQ ID NO 20
<211> LENGTH: 24
<212> TYPE: DNA
<213> ORGANISM: Artificial Sequence
<220> FEATURE:
<223> OTHER INFORMATION: 6p24.3  reverse primer

<400> SEQUENCE: 20
atatggcctg aaagacctcg cact                                         24

<210> SEQ ID NO 21
<211> LENGTH: 24
<212> TYPE: DNA
<213> ORGANISM: Artificial Sequence
<220> FEATURE:
<223> OTHER INFORMATION: 1q32.2  forward primer(2)

<400> SEQUENCE: 21
agtgctttaa gggtgcgttg ttgg                                         24

<210> SEQ ID NO 22
<211> LENGTH: 24
<212> TYPE: DNA
<213> ORGANISM: Artificial Sequence
<220> FEATURE:
<223> OTHER INFORMATION: 1q32.2  reverse primer(2)

<400> SEQUENCE: 22
actttcacag cacctccaca gact                                         24

<210> SEQ ID NO 23
<211> LENGTH: 24
<212> TYPE: DNA
<213> ORGANISM: Artificial Sequence
<220> FEATURE:
<223> OTHER INFORMATION: 13q13.1 forward primer(2)

<400> SEQUENCE: 23
aggcattccc acatgcacaa acag                                         24
```

```
<210> SEQ ID NO 24
<211> LENGTH: 24
<212> TYPE: DNA
<213> ORGANISM: Artificial Sequence
<220> FEATURE:
<223> OTHER INFORMATION: 13q13.1 reverse primer(2)

<400> SEQUENCE: 24
agttcactgc agtcaccctt ggaa                                          24

<210> SEQ ID NO 25
<211> LENGTH: 24
<212> TYPE: DNA
<213> ORGANISM: Artificial Sequence
<220> FEATURE:
<223> OTHER INFORMATION: 14q24.2 forward primer(2)

<400> SEQUENCE: 25
aacccacaag cagaggaagg agaa                                          24

<210> SEQ ID NO 26
<211> LENGTH: 24
<212> TYPE: DNA
<213> ORGANISM: Artificial Sequence
<220> FEATURE:
<223> OTHER INFORMATION: 14q24.2 reverse primer(2)

<400> SEQUENCE: 26
atgtgtgtgg tgctgacatt gctg                                          24

<210> SEQ ID NO 27
<211> LENGTH: 51
<212> TYPE: DNA
<213> ORGANISM: Artificial Sequence
<220> FEATURE:
<223> OTHER INFORMATION: SNP marker_rs27037

<400> SEQUENCE: 27
attattatta ttacaattgt tagggktgtt ttttcttttta gaaattcaaa g           51

<210> SEQ ID NO 28
<211> LENGTH: 51
<212> TYPE: DNA
<213> ORGANISM: Artificial Sequence
<220> FEATURE:
<223> OTHER INFORMATION: SNP marker_rs27434

<400> SEQUENCE: 28
agtgtgaatg agcttatacc tggtgrgcca gttcatgggc cacagtcatt g            51

<210> SEQ ID NO 29
<211> LENGTH: 51
<212> TYPE: DNA
<213> ORGANISM: Artificial Sequence
<220> FEATURE:
<223> OTHER INFORMATION: SNP marker_rs10865331

<400> SEQUENCE: 29
actgactttg gtgccgtatc taccargtgg tcaagctgat gccattgcaa g            51

<210> SEQ ID NO 30
<211> LENGTH: 51
<212> TYPE: DNA
<213> ORGANISM: Artificial Sequence
<220> FEATURE:
<223> OTHER INFORMATION: SNP marker_rs27044
```

<400> SEQUENCE: 30
tgcacacagg cgaggagtag tagttsactc cgcagcattc gctctgagac t        51

<210> SEQ ID NO 31
<211> LENGTH: 51
<212> TYPE: DNA
<213> ORGANISM: Artificial Sequence
<220> FEATURE:
<223> OTHER INFORMATION: SNP marker_rs30187

<400> SEQUENCE: 31
tgtgatggtt attaggggaa aacccytctg cagtgtccaa gtgttcatca t        51

<210> SEQ ID NO 32
<211> LENGTH: 43
<212> TYPE: DNA
<213> ORGANISM: Artificial Sequence
<220> FEATURE:
<223> OTHER INFORMATION: a partial of 1q32.2 CNV region showing a
      partial of the deleted region

<400> SEQUENCE: 32
taactaggga taataacggc taaagtgatt aatgctttcc ccc                 43

<210> SEQ ID NO 33
<211> LENGTH: 22
<212> TYPE: DNA
<213> ORGANISM: Artificial Sequence
<220> FEATURE:
<223> OTHER INFORMATION: a partial of 1q32.2 CNV region

<400> SEQUENCE: 33
taaactaggg atgctttccc cc                                        22

<210> SEQ ID NO 34
<211> LENGTH: 41
<212> TYPE: DNA
<213> ORGANISM: Artificial Sequence
<220> FEATURE:
<223> OTHER INFORMATION: a partial of 13q13.1 CNV region showing a
      partial of the deleted region

<400> SEQUENCE: 34
gggatgttgg ctggggtaga taggacctgg gcttcatcat c                   41

<210> SEQ ID NO 35
<211> LENGTH: 20
<212> TYPE: DNA
<213> ORGANISM: Artificial Sequence
<220> FEATURE:
<223> OTHER INFORMATION: a partial of 13q13.1 CNV region

<400> SEQUENCE: 35
gggatgttgg cttcatcatc                                           20

<210> SEQ ID NO 36
<211> LENGTH: 43
<212> TYPE: DNA
<213> ORGANISM: Artificial Sequence
<220> FEATURE:
<223> OTHER INFORMATION: a partial of 14q24.2 CNV region showing a
      partial of the deleted region

<400> SEQUENCE: 36
aagaataaaa agtacccatt ttttccgtaa aagtaattta tga                 43

```
<210> SEQ ID NO 37
<211> LENGTH: 22
<212> TYPE: DNA
<213> ORGANISM: Artificial Sequence
<220> FEATURE:
<223> OTHER INFORMATION: a partial of 14q24.2 CNV region

<400> SEQUENCE: 37
aagaataaaa agtaatttat ga                                          22
```